(12) United States Patent
Milligan et al.

(10) Patent No.: US 7,741,064 B2
(45) Date of Patent: *Jun. 22, 2010

(54) MATERIALS AND METHODS RELATING TO G-PROTEIN COUPLED RECEPTOR OLIGOMERS

(75) Inventors: Graeme Milligan, Hyndland (GB); Dominic Behan, San Diego, CA (US)

(73) Assignee: The University Court of the University of Glasgow, Glawgow (GB)

( * ) Notice: Subject to any disclaimer, the term of this patent is extended or adjusted under 35 U.S.C. 154(b) by 17 days.

This patent is subject to a terminal disclaimer.

(21) Appl. No.: 12/119,401

(22) Filed: May 12, 2008

(65) Prior Publication Data

US 2008/0286828 A1 Nov. 20, 2008

Related U.S. Application Data

(63) Continuation of application No. 10/555,709, filed as application No. PCT/GB2004/002150 on May 18, 2004, now Pat. No. 7,405,053.

(60) Provisional application No. 60/472,025, filed on May 20, 2003.

(51) Int. Cl.
C07K 14/705 (2006.01)
C07K 19/00 (2006.01)
C12N 15/62 (2006.01)
G01N 33/566 (2006.01)

(52) U.S. Cl. ................ 435/7.2; 435/7.21; 435/69.7; 436/501; 536/23.4

(58) Field of Classification Search ............ None
See application file for complete search history.

(56) References Cited

U.S. PATENT DOCUMENTS

| | | | |
|---|---|---|---|
| 5,462,856 | A | 10/1995 | Lerner et al. |
| 6,051,386 | A | 4/2000 | Lerner et al. |
| 6,365,356 | B1 | 4/2002 | Gershengorn |
| 6,468,756 | B1 | 10/2002 | Bonini et al. |
| 6,555,339 | B1 | 4/2003 | Liaw et al. |
| 7,105,308 | B2 | 9/2006 | Chan-Hui et al. |
| 7,119,190 | B2 | 10/2006 | Liaw et al. |
| 2001/0053848 | A1 | 12/2001 | Patel et al. |
| 2002/0137054 | A1 | 9/2002 | Aubart et al. |

FOREIGN PATENT DOCUMENTS

WO WO 98/46995 10/1998

OTHER PUBLICATIONS

Carrillo, et al. Dimers of class A G protein-coupled receptors function via agonist-mediated trans-activation of associated G proteins. The Journal of Biological Chemistry, 2003, vol. 278, No. 43, pp. 42578-42587.

Carrillo, et al. Measurement of agonist-dependent and -independent signal initation of $\alpha_{1b}$—adrenoceptor mutants by direct analysis of guanine nucleotide exchange on the G protein $G\alpha_{11}$. The Journal of Pharmacology and Experimental Therapeutics, 2002, vol. 302, No. 3, pp. 1080-1088.

Duthey, et al. A single subunit (GB2) is required for G-protein activation by the heterodimeric $GABA_B$ receptor. The Journal of Biological Chemistry, 2002, vol. 277, No. 5, pp. 3236-3241.

George, et al. G-protein-coupled receptor oligomerization and its potential for drug discovery., Nature Reviews, Drug Discover, 2002, vol. 1, No. 10, pp. 808-820.

Greasley et al. Mutational and computational analysis of the $\alpha 1b$—Adrenergic Receptor. The Journal of Biological Chemistry, 2001, vol. 276, No. 49, pp. 42486-46494.

Hebert et al. Structural and functional aspects of G protein-coupled receptor oligomerization. Biochemistry and Cell Biology, 1998, vol. 76, pp. 1-11.

Ji et al. Cis- and trans-activation of hormone receptors: the LH receptor. Molecular Endocrinology, 2002, 16(6): 1299-1308.

Lee et al. Ophan G. protein-coupled receptors in the CNS. Current Opinion in Pharmacology, 2001, vol. 1, pp. 31-39.

Lee et al. Two defective heterozygous luteinizing hormone receptors can rescue hormone action. The Journal of Biological Chemistry, 2002, vol. 277, No. 1, pp. 15795-15800.

Milligan, et al. Oligomerisation of G-protein-coupled receptors. Journal of Cell Science, 2001, vol. 114, No. Pt. 7, pp. 1265-1271.

Milligan, et al. Prinicples: Extending the utility of [$^{35}$S]GTP $\gamma$S binding assays. Trends in Pharmacological Sciences, Elsevier, 2003, vol. 24, No. 2, pp. 87-90.

Molinari et al. Promiscuous coupling at receptor-$G\alpha$ fusion proteins. The Journal of Biological Chemistry, 2003, vol. 278, No. 18, pp. 15778-15788.

Osugai et al. Co-expression of defective luteinizing hormone receptor fragments partially reconstitutes ligand-induced signal generation. Journal of Biological Chemistry, 1997, vol. 272, No. 40, pp. 25006-25012.

Seifert et al. GPCR- $G\alpha$ fusion proteins: molecular analysis of receptor-G-protein coupling. Trends in Pharmacological Sciences, Elsevier Trends Journal, Cambridge, 1999, vol. 20, No. 9, pp. 383-389.

Vassilatais et al. The G protein-coupled receptor repertoires of human and mouse. Proceedings of the National Academy of Sciences, 2003, vol. 100, No. 8, pp. 4903-4908.

Wess et al. Molecular basis of receptor/G-protein-coupling selectivity. Pharmacology and Therapeutics, 1998, vol. 80, No. 3, pp. 231-264.

*Primary Examiner*—John D Ulm
(74) *Attorney, Agent, or Firm*—James S. Keddie; Bozicevic, Field & Francis LLP

(57) ABSTRACT

The invention provides materials and methods relating to G-protein coupled receptor (GPCR) oligomers. Complexes of two or more GPCRs associated with G-proteins are provided. Also provided are fusion proteins comprising a GPCR and a G-protein, nucleic acids, expression vectors and host cells. Methods of producing the complexes and fusion proteins of the invention are also provided.

11 Claims, 14 Drawing Sheets

| GPCR | specie | G protein | Aminoacid sequence (2nd intracelular loop) |
|---|---|---|---|
| 5HT1A receptor | human | Gi/Go | DRYWAITDPID |
| 5HT1B receptor | mouse | Gi/Go | DRYWAITDAVE |
| 5HT1D receptor | rabbit | Gi/Go | DRYWAITDALE |
| 5HT2A receptor | rat | Gq/G11 | DRYVAIQNPIH |
| 5HT2C receptor | rat | Gq/G11 | DRYVAIRNPIE |
| 5HT4 receptor | mouse | Gs | DRYYAICCQPL |
| 5HT6 receptor | rat | Gs | DRYLLILSPIR |
| α1a adrenergic receptor | bovine | Gq/G11 | DRYIGVSYPIR |
| α1b adrenergic receptor | hamster | Gq/G11 | DRYIGVRYSLQ |
| α2b adrenergic receptor | rat | Gi/Go | DRYWAVSRALE |
| β1 adrenergic receptor | human | Gs | DRYLAITSPFR |
| β2 adrenergic receptor | bovine | Gs | DRYLAITSPFK |
| β3 adrenergic receptor | mouse | Gs | DRYLAVTNPLR |
| A1 adenosine receptor | human | Gi/Go | DRYLRVKIPLR |
| A3 adenosine receptor | human | Gi/Go | DRYLRVKLTVR |
| M1 receptor | mouse | Gq/G11 | DRYFSVTRPLS |
| M2 receptor | human | Gi/Go | DRYFCVTKPLT |
| M3 receptor | mouse | Gi/Go | DRYFSITRPLT |
| Melanocortin2 receptor | human | Gs | DRYITIFHALR |
| AT1A receptor | human | Gq/G11 | DRYLAIVHPMK |
| AT1B receptor | rat | Gq/G11 | DRYLAIVHPMK |
| B2 bradikinin receptor | human | Gq/G11 | DRYLALVKTMS |
| CXCR3 | mouse | Gi/Go | DRYLSIVHATQ |
| CXCR4 | human | Gi/Go | DRYLAIVHATN |
| D2 receptor | mouse | Gi/Go | DRYTAVAMPML |
| D3 receptor | rat | Gi/Go | DRYTAVVMPVH |
| FSHR | bovine | Gs | ERWHTITHAMQ |
| GRHR | mouse | Gq/G11 | DRSLAITQPLA |
| H1 receptor | mouse | Gq/G11 | DRYRSVQQPIR |
| H2 receptor | human | Gs | DRYCAVMDPLR |
| LSHR | mouse | Gs | ERWHTITYAVQ |
| δ opioid receptor 1 | rat | Gi/Go, Gz | DRYIAVCHPVK |
| κ opioid receptor 1 | mouse | Gi/Go | DRYIAVCHPVK |
| μ opioid receptor 1 | rat | Gi/Go, Gz | DRYIAVCHPVK |
| rhodopsin | bovine | Gt | ERYVVVCKPMS |
| Oxytocin receptor | rat | Gq/G11 | DRCLAICQPLR |
| P2U purinoceptor 1 | rat | Gq/G11 | HRCLGVLRPIH |
| Prostaglandin D2 receptor | mouse | Gs | ECWLSLGHPFF |
| Prostaglandin E2 recptor(E1) | rat | Gq/G11 | ERCVGVTQPLI |
| Somatostatin receptor 2 | human | Gi/Go Gq | DRYLAVVHPIK |
| TRH receptor | rat | Gq/G11 | ERYIAICHPIK |
| Vasopresin 1A receptor | | Gq/G11 | DRYIAVCHPLK |

Figure 3

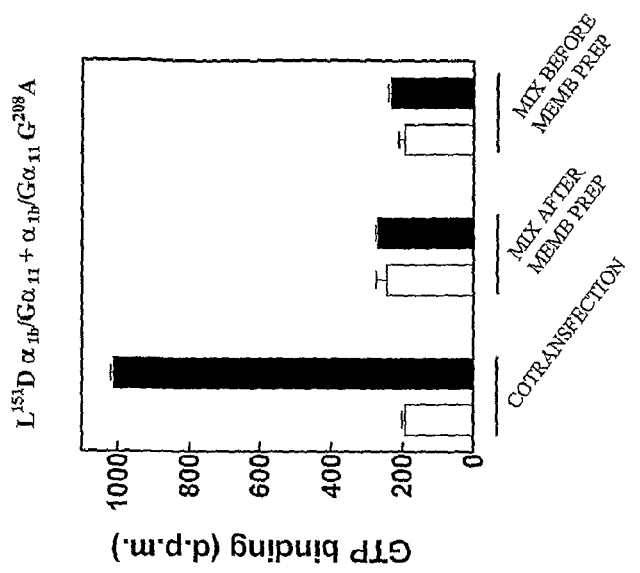
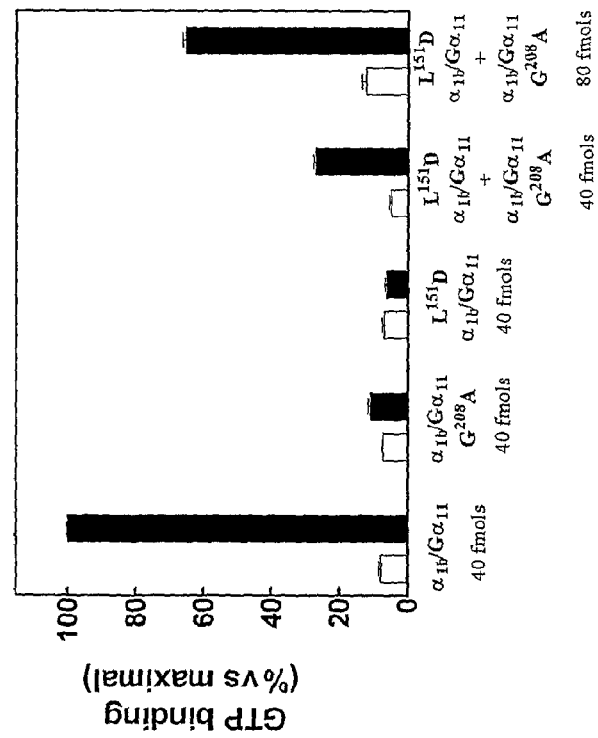
Figure 4
Reconstitution of GTPγS binding by crosstalk between fusion proteins A
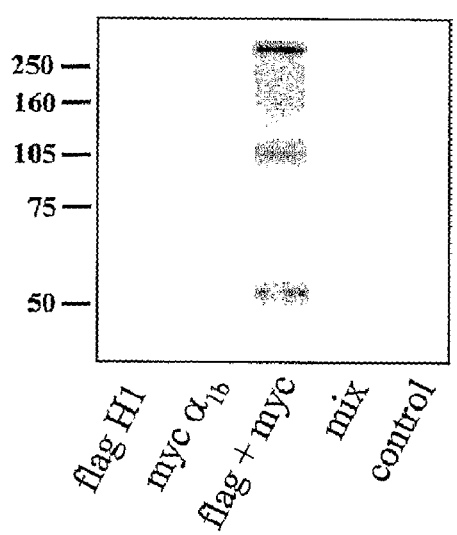
B
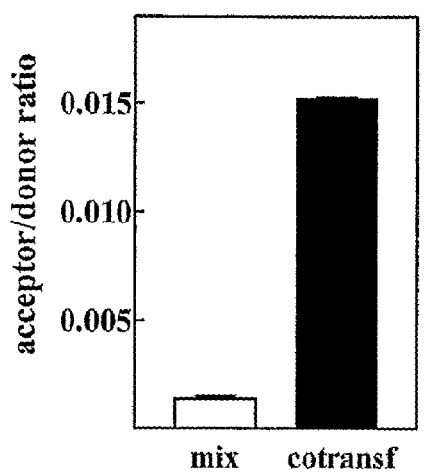
Figure 11

MATERIALS AND METHODS RELATING TO G-PROTEIN COUPLED RECEPTOR OLIGOMERS

FIELD OF THE INVENTION

The present invention concerns materials and methods relating to G-protein coupled receptor (GPCR) oligomers. Particularly, but not exclusively, the invention provides biological reagents comprising the GPCR oligomers, methods of producing said biological reagents and assays for determining their function. The invention also provides assays for determining compounds that have the ability to modulate the function of GPCR oligomers, particularly hetero-oligomers.

BACKGROUND OF THE INVENTION

GPCRs are one of the largest gene families in the human genome and have been the most tractable set of targets for the development of clinically effective, small molecule, medicines. It is estimated that of the drugs used clinically in man some 40% target GPCRs. There is thus great interest in the details of the structure, regulation and activation mechanisms of GPCRs as well as the downstream signalling cascades they control. The class A or rhodopsin-like family of GPCRs is by far the largest containing more than 80% of the total GPCR family members. More than 800 genes encoding GPCRs have been identified in the human genome sequencing programme but only some 25 of these are currently the target for clinically effective medicines. There is thus great potential to expand this and to find useful medicines that target recently identified GPCRs (Lee et al., 2001).

In the recent past, the concept that GPCRs exist as dimers has moved rapidly from hypothesis to clearly accepted (see Bouvier, 2001, Milligan, 2001, George et al., 2002 for reviews). Although homodimers (i.e. a dimer containing two copies of one individual GPCR) have been the best studied, growing evidence suggests that heterodimerisation (i.e. the dimer consists of one molecule of each of two different GPCRs) both occurs and can have both functional and pharmacological sequelae (Devi, 2001, George et al., 2002). However, important questions remain in relation to the selectivity of formation of such heterodimers and how to monitor the function of a heterodimer in isolation when co-expression of two different GPCRs must also result in the production of homodimeric pairs. Given that many GPCRs are co-expressed in a single cell then it is likely that the complement of GPCR dimers in a cell is complex.

Studies have been carried out on the γ-aminobutyric acid (GABA) type B receptor (GABA$_B$R) (Duthey et al., 2002). This is an unusual GPCR because it is the only one known to date that needs two subunits, GB1 and GB2, to function. The GB1 subunit contains the GABA binding site but is unable to activate G-protein alone. GB2 does not bind GABA but does have the ability to activate G-proteins. Duthey et al. looked at the role of each subunit within the GB1-GB2 heteromer in G-protein coupling. The study included introducing mutations into both GB1 and GB2, particularly within the third intracellular loop. They determined that mutation to GB2 prevents G-protein activation, whereas a similar mutation to GB1 did not affect receptor function. Although interesting for the GABA$_B$ receptor, this study unfortunately does not provide any information on GPCRs where the same protein is responsible for both ligand binding and G-protein activation.

Further studies looked at the co-expression of a first mutant receptor which was defective in hormone binding and a second mutant receptor which was defective in signal generation. It was reported that co-expression of the two mutants rescued hormone-activated cAMP production (Lee et al., J. Biol. Chem. Vol. 277, No. 18, 2002; Osuga et al., J. Biol. Chem. Vol. 272, No. 40, 1997).

However, although it is acknowledged that GPCRs are extremely important as potential drug targets, there does not exist a satisfactory screening assay which allows reliable data to be gathered about the functional properties, e.g. ligand binding properties, of potentially naturally occurring GPCR oligomers, particularly GPCR hetero-oligomers.

SUMMARY OF THE INVENTION

The present inventor has surprisingly found that, following ligand binding, a GPCR has the ability to activate a G-protein that is associated with a second GPCR, in situations where both GPCRs have formed an oligomer.

Specifically, and as illustrated by the examples given below, the inventor has found that co-expression in a cell of (A) a fusion protein of a GPCR and a G-protein where the GPCR is rendered non-functional with respect to the G-protein and (B) a fusion protein of a GPCR and a G-protein where the G-protein is rendered non-functional, i.e. cannot act on a signal received by the GPCR, produces the following complexes, A, B, AA, BB, AB and BA where only AB and BA are functional, i.e. G-protein is activated to bind GTP and initiate the GPCR signalling cascade.

The basic strategy takes advantage of the fact that GPCR/G-protein α subunit fusion proteins (Milligan, 2000; Milligan, 2002) can be considered as bi-functional polypeptides containing the sequences and the functional properties of both elements i.e. the GPCR and the G-protein. By generating pairs of distinct mutants in which the first is mutated in the GPCR to render it incapable of activating a wild type G-protein to which it is fused and the second is mutated in the G-protein such that it cannot be activated by a wild type GPCR linked to it, the present inventor demonstrates that function may be restored when the two mutants are co-expressed. Thus, only the oligomer comprising at least each mutant produces functional complementation and is able to generate a signal in response to agonist ligands.

The inventor has appreciated that this phenomenon can be utilised to provide reliable screening assays to determine the properties of GPCR oligomers, particularly hetero-oligomers, and to provide biological reagents for using in such assays.

Thus, at its most general, the present invention provides materials and methods for determining the functional properties of GPCR oligomers, including determining potential ligands. The term GPCR is well understood in the art and refers to any cell surface trans-membrane protein, that when activated by a suitable compound, in turn activates a guanine nucleotide-binding protein (G-protein).

In a first aspect of the present invention, there is provided a biological reagent comprising a GPCR oligomer having
 (a) a first GPCR associated with a first G-protein wherein the first GPCR is non-functional with respect to the associated first G-protein;
 (b) a second GPCR associated with a second G-protein wherein the second G-protein is non-functional.

By the term "non-functional" it is meant that, in contrast to the wild-type, the protein (GPCR or G-protein) is not able to carry out a particular biological function. Thus, the fact that GPCR is non-functional with respect to O-protein means that it is incapable of carrying out its wild type biological function with respect to G-protein, namely, to activate G-protein following ligand binding. Other biological functions characteristic of the wild type (e.g. ligand binding) are preferably maintained.

Likewise, the non-functional G-protein is incapable of carrying out its wild type biological function, namely, initiating a cellular signalling cascade following stimulation from the GPCR.

The ability of the first and second GPCRs to form an oligomer, brings the functional second GPCR into the environment of the functional first G-protein. The functional GPCR is then able to activate the functional G-protein which in turn brings about the cellular signalling cascade.

The first and second GPCRs may be the same, i.e. a homo-oligomer, e.g. a homodimer, homotrimer or higher order oligomer, or the first and second GPCRs may be different, i.e. a hetero-oligomer, e.g. a heterodimer, heterotrimer or higher order oligomer.

Ideally, the oligomer is present in a cell membrane. This may conveniently be achieved if the first and second GPCRs and their associated G-proteins are co-expressed in the cell. Thus, ideally the GPCRs and their G-proteins are associated with each other as fusion proteins. However, the skilled person will appreciate that other means of association are possible. For example, the proteins may be brought together by coupling means such as binding pairs, chemical bonds etc, or simply by natural association in a cellular environment.

The present invention also provides a mutant GPCR/native G-protein fusion protein for use in producing a biological reagent in accordance with the first aspect, and particularly for use in the methods according to the present invention (i.e. comprising a modified non-functional GPCR/functional G-protein), as well as a corresponding nucleic acid construct. Minor modifications may be carried out to the protein sequence, for example, an epitope tag may be added to the N-terminus of the receptor, a spacer segment introduced, in order to create a gap between the GPCR protein sequence and the G-protein sequence and/or a terminal methionine of the G-protein gene removed. Many such modifications may be envisaged by the skilled addressee providing the functionality in use of the receptor/G-protein fusion protein remains substantially unaffected.

Further, the present invention provides use of a mutant GPCR/G-protein fusion protein, as described herein, in the methods according to the present invention (i.e. comprising either a modified non-functional GPCR/functional G-protein, or functional GPCR/non-functional G protein).

The nucleic acid constructs of the present invention comprise nucleic acid, typically DNA, RNA, mRNA or cDNA encoding the particular receptor to which is fused, in-frame, the appropriate nucleic acid sequence encoding the G-protein. Generally speaking the nucleic acid constructs are expressed in the cells by means of an expression vector.

Accordingly, there is also provided a cell comprising a GPCR oligomer having
 (a) a first GPCR associated with a first G-protein wherein the first GPCR is non-functional with respect to the associated first G-protein;
 (b) a second GPCR associated with a second G-protein wherein the second G-protein is non-functional.

Typically, the cells are of eukaryotic origin, including yeast, such as vertebrate origin, including amphibian, and mammalian (especially human) and the expression vector chosen is one which is suitable for expression in the particular cell type. Suitable cells and expression vectors are discussed in more detail below.

In order that the biological reagent can be used in assays to determine the natural properties of the GPCRs oligomers, it is important that any ligand binding sites present on the GPCRs are maintained. Thus, it is preferable that the first GPCR is rendered non-functional only with respect to the associated first G-protein. In other words, the first GPCR maintains any ability it had to bind ligand but is incapable of activating G-protein following ligand binding. Of course, the actual combination of the GPCRs may alter the properties of the ligand binding sites, but this will be a reflection of what would happen naturally following oligomerization formation and should not be as a result of artificial manipulation.

With regard to the second G-protein, it is preferable that this is rendered non-functional at least with respect to the second GPCR, i.e. such that is cannot act on a signal sent by the GPCR. Thus, in order for the biological reagent to be useful in assays, it is important that the second G-protein is rendered non-functional at least to the extent that it is incapable of activating a cellular signal, i.e. unable to functionally bind GTP and initiate the GPCR signalling cascade.

The present inventor has found that for $G_{11\alpha}$ G-protein, glycine 208, which is common to these G-proteins, may be mutated, e.g. by substitution, in order to render the G-protein non-functional.

Accordingly, it is preferable to modify the second G-protein by at least one amino acid substitution where said at least one amino acid is glycine equivalent to glycine 208 in $G_{11\alpha}$.

As mentioned above, it is preferable that the first GPCR is modified so as to render it non-functional only with respect to the G-protein. The field of molecular biology has advanced such that it is possible to modify a protein's amino acid sequence very specifically so as to maintain some functions (e.g. ability to bind ligand) while disrupting others (e.g. ability to activate G-protein). The present inventor has found that the highly conserved residues in the $2^{nd}$ intracellular loop of the GPCR are particularly suitable for mutation as these render the receptor substantially non-functional with respect to its associated G-protein. Specifically, the inventor has found that mutation of one or more residues in this region renders the GPCR non-functional with respect to G-protein (i.e. G-protein is not activated) but still able to bind ligand. Mutations to the GPCR are discussed in more detail below.

In a second aspect of the present invention, there is provided a method of producing a biological reagent according to the first aspect, said method comprising the steps of
 (a) producing or providing a first nucleic acid construct encoding a fusion protein of a first GPCR and a first G-protein wherein the first GPCR is mutated as compared to the wild-type such that it is non-functional with respect to the fused G-protein;
 (b) producing or providing a second nucleic acid construct encoding a fusion protein of a second GPCR and a second G-protein wherein the second G-protein is mutated as compared to the wild-type rendering it non-functional;
 (c) co-expressing the first and second nucleic acid constructs in a cell so as to produce a GPCR oligomer comprising said first and second GPCRs.

If the first and second nucleic acid construct had already been produced, then the method may simply comprise the steps of
 (a) expressing a first nucleic acid construct in a cell, said nucleic acid construct encoding a first GPCR/G-protein fusion protein wherein the GPCR is mutated as compared to the native GPCR thereby rendering it non-functional with respect to its G-protein;
 (b) expressing a second nucleic acid construct in said cell, said second nucleic acid construct encoding a second GPCR/G-protein fusion protein wherein the G-protein is mutated as compared to the native G-protein thereby rendering it non-functional;

(c) allowing said first and second fusion proteins to assemble into a GPCR oligomer in the cell membrane.

The method may further comprise the step of isolating a part of the cell membrane comprising said complex. This may be achieved by lysing the cell and isolating the cell membrane.

As mentioned above, the first GPCR and the second GPCR may be the same (homo-oligomer) or different (hetero-oligomer).

The present inventor believes that in order for the first and second GPCRs to form an oligomer, they must have some affinity for each other. Accordingly, the inventor has devised a method by which this may be determined. Thus, as a third aspect of the invention, there is provided a method of determining a first and second GPCR having affinity for each other such that they form a complex (GPCR oligomer), said method comprising the steps of (a) producing or providing a first nucleic acid construct encoding a first GPCR and its associated G-protein as a fusion protein wherein the GPCR is mutated as compared to the wild-type so that it is non-functional with respect to its associated G-protein;

(b) producing or providing a second nucleic acid construct encoding a second GPCR and its associated G-protein wherein the G-protein is mutated as compared to the wild-type G-protein so that it is non-functional;

(c) co-expressing said first and second nucleic acid constructs in a cell; and (d) determining the presence of a complex comprising said first and second GPCRs.

The presence of a GPCR oligomer comprising said first and second GPCRS may be determined by contacting the cell with a ligand for said second GPCR and determining whether said first G-protein is activated.

As before, the first and second GPCRs may be different. Where they are different, it is preferably that they occur naturally on the same cell. This makes it reasonable to predict that the oligomer may be formed in nature. For this reason, the method may further comprise the initial step of determining which GCPRs are present on a particular cell type i.e. which are endogenous to the same cell. As many GPCRs have been fully characterised, this may be achieved by screening the gene products of a particular cell, e.g. a chip based screen or techniques such as rt-PCR followed by sequencing.

The determination of GPCRs that have affinity for each other, i.e. are capable of forming oligomers, is of great importance pharmacologically. For example, the ability of two receptors to form oligomers, (hetero or homo) may be tissue specific. Thus, these tissue specific GPCR oligomers may form important drug targets. Table 1 indicates an exemplary medical implication which may be associated with each cell type.

The production of biological reagents in accordance with the present invention, for the first time opens up the possibility of various screening assays which provide convenient and reliable ways to determine the function of the oligomer, particularly with regard to ligand binding and the subsequent cellular signalling cascade.

For example, in a fourth aspect of the invention, there is provided a method of detecting an effect a compound has on a GPCR oligomer, comprising the steps of:

a) providing a cell or cell membrane comprising a biological reagent in accordance with the first aspect of the invention;

b) contacting the compound with said cell or cell membrane; and c) observing an effect said compound has on the GPCR oligomer, particularly on the signalling of the GPCR oligomer.

Also in accordance with this aspect of the invention, there is provided a method of identifying a compound capable of interacting with a GPCR oligomer, said method comprising the steps of a) producing a cell expressing a GPCR oligomer comprising (i) a first GPCR associated with a first G-protein wherein the first GPCR is non-functional with respect to the associated first G-protein; (ii) a second GPCR associated with a second G-protein wherein the second G-protein is non-functional;

b) contacting said cell or isolated cell membrane thereof with said compound;

c) determining whether said compounds interacts with the GPCR oligomer.

It is to be understood that the cell or cell membrane comprising the GPCR oligomer can also comprise non-functional, or a substantially non-functional GPCRs e.g. a monomer comprising either the first or second GPCR (i or ii), a dimer of the first GPCR (i/i), or a dimer of the second GPCR (ii/ii). The advantage of the present invention is that the formation of these monomers or dimers does not affect the results of the screening method because, owing to the mutations made to the first and second GPCRs, the only functional receptor (able to stimulate G-protein and initiate a signalling cascade) is the oligomer comprising at least both the first and the second GPCR. Thus, any monomer or homo-oligomer (i.e. both first GPCRs or both second GPCRs) will have no activity, other than perhaps background activity, compared to the oligomer comprising at least both a first GPCR and a second GPCR.

Background activity is understood to mean less than 20%, 15%, 10% or preferably 5% of native or wild type activity.

Interaction of the compound under test with the GPCR oligomer may result in one or more of a number of biological events. For example, interaction may result in a conformational change in the ligand binding site. This may alter the potency of the receptor's natural ligands. Alternatively, interaction between the compound and the GPCR oligomer may result in a cellular receptor signalling cascade indicating that the compound is a potential agonist. The compound may bind to a ligand binding site present on the native GPCR monomers or it may bind to a new binding site created as a result of GPCR oligomerization.

A method according to the fourth aspect of the invention may be used to determine new ligands (agonists, antagonists etc) which are able to bind the GPCR oligomer. It may be that these ligands are different to those able to bind the GPCR oligomer. It may be that these ligands are different to those able to bind and activate the corresponding GPCR monomers, or it may be that the effect of binding may be different compared to that of the individual monomer. For example, ligand binding to the oligomer, as opposed to the corresponding monomers may result in an altered signal, e.g. increased or decreased, or it may result in a different cellular pathway being activated. These receptor oligomer properties may all be determined using the method according to the fourth aspect.

Further, the compound under test may have the ability to block a known ligand, e.g. an agonist, of the GPCR oligomer. In order to determine this, the compound may be contacted with the cell in the presence of the known ligand, and the ability of the ligand to activate the GPCR compared to its ability to activate the GPCR in the absence of said compound.

Accordingly, the invention further provides a method of identifying a compound having the ability to modulate binding between a GPCR oligomer and its ligand, said method comprising
  a) producing or providing a cell expressing a GPCR oligomer comprising (i) a first GPCR associated with a first G-protein where the first GPCR is non-functional with respect to the associated first G-protein; (ii) a second GPCR associated with a second G-protein wherein the second G-protein is non-functional;
  b) contacting said cell with said compound in the presence of said ligand
  c) comparing the ability of said ligand to bind GPCR oligomer with the ability of said ligand to bind the GPCR under comparable conditions but in the absence of said compound.

Thus, the compound may have the ability to competitively inhibit binding of the ligand to the GPCR or it may in fact result in increased binding and/or increased receptor stimulation as a result of ligand binding, i.e. it increases ligand potency.

One possibility is that a third GPCR may complex with the GPCR oligomer and have an allosteric effect. This may be determined by the above method when the compound is a third GPCR. In this situation, it is preferable that the wild-type third GPCR along with the wild-type first and second GPCRs, are endogenously co-expressed in at least one cell type.

As mentioned above, it is possible that when two GPCRs form an oligomer, their respective ligand binding sites may be altered and/or new ligand binding sites formed. These may have great pharmacological importance. Therefore the present invention further provides, as a fifth aspect, a method for determining the presence of a new or altered ligand binding site on a GPCR oligomer which is not present on the corresponding monomer(s), said method comprising the steps of
  a) contacting a compound with a first cell expressing a GPCR complex having (i) a first GPCR associated with a G-protein wherein the first GPCR is modified such that it is non-functional with respect to said G protein; and (ii) a second GPCR associated with a G-protein wherein the G-protein is modified so that it is non-functional;
  b) contacting said compound with a second cell expressing an unmodified first GPCR monomer; and
  c) comparing the effect of the compound on the first cell and the second cell to determine the presence of a new or altered ligand binding site created by the GPCR oligomer.

Where the GPCR oligomer is a hetero-oligomer, i.e. it comprises at least two different GPCRs, the method may further comprise the step of contacting the compound with a third cell expressing an unmodified second GPCR monomer, and again, comparing the effect of the compound on the third cell to determine the presence or a new or altered ligand binding site being created as a result of oligomerization of two or more GPCRs.

Preferably, the unmodified (i.e. functional) first and second GPCR monomers are expressed in said second or third cell respectively by recombinant means.

The presence of a new ligand binding site may be determined by the fact that a particular compound is able to cause a receptor signalling cascade in the cell on contact with the oligomer but not on contact with the corresponding monomer(s).

The presence of an altered ligand binding site may be determined by the fact that the receptor signalling cascade is altered as between the oligomer and the corresponding monomer(s), e.g. the signal is increased or decreased, and/or the signalling pathway is altered.

The "effect" of the compound on the first or second cell includes its ability to bind to the GPCR oligomer (determined, for example, by labelling the compound) and its ability to initiate a cellular signalling cascade (determined, for example, by detecting changes in the activity of compounds of the signalling pathway).

Even if the various ligand binding sites remain unchanged following receptor oligomerization, other changes in receptor function may occur.

Accordingly, the present invention further provides a method for determining a change in GPCR function as a result of forming a GPCR oligomer, said method comprising
  (a) contacting a compound with a first cell expressing a GPCR oligomer having (i) a first GPCR associated with a G-protein wherein the first GPCR is modified such that it is non-functional with respect to said G-protein; and (ii) a second GPCR associated with a G-protein wherein the G-protein is modified so that it is non-functional;
  (b) contacting said compound with a second cell expressing an unmodified first GPCR and/or a second cell expressing an unmodified second GPCR; and
  (c) comparing the function of said GPCR oligomer with that of said unmodified first GPCR and/or with that of said second GPCR to determine a change in receptor function resulting from oligomerization.

In the methods described above for determining compounds capable of activating a GPCR oligomer (e.g. in accordance with the fourth aspect) and for determining the presence of a new or altered ligand binding site caused by GPCR oligomerisation (e.g. in accordance with the fifth aspect), the skilled person may choose to add additional mutations to the first and second GPCR to additionally determine changes in ligand binding. The manipulation of the GPCR protein is well within the capabilities of the skilled person. For example, for all aspects of the present invention, it may be possible to additionally modify the GPCR fusion proteins into a constitutively active form. Examples of methods for constitutively activating GPCR sequences are provided in U.S. Pat. No. 6,555,339 (incorporated herein by reference) and PCT/US98/07496, WO 98/46995 (incorporated herein by reference).

The biological reagents in accordance with the present invention also allows the determination of differential G-protein coupling as between monomers, homo-oligomers and hetero-oligomers.

By way of example, the present invention allows a method to be carried out in order to evaluate if homodimers (e.g. AA or BB) couple to a different G protein than a heterodomer (e.g. AA or BA), comprising the steps of
  (a) producing or providing a plurality of fusion proteins each comprising one GPCR (e.g. A and B) fused to one of a plurality of different G proteins covering all major G-protein classes (e.g. Gs, Gq and Gi). For example one pair will contain a receptor which is render inactive by mutation in the second intracellular loop which is fused to Gs. The second receptor in this pair will have a functional receptor fused to a mutated Gs such that the mutation renders the G protein inactive.

The second pair will contain a receptor which is render inactive by mutation in the second intracellular loop which is fused to Gq. The second receptor in this pair will have a functional receptor fused to a mutated Gq such that the mutation renders the G protein inactive.

The third pair will contain a receptor which is render inactive by mutation in the second intracellular loop which is fused to Gi. The second receptor in this pair will have a functional receptor fused to a mutated Gi such that the mutation renders the G protein inactive.

Other G proteins such as G12 and G13 may be evaluated in a similar fashion.

(b) producing or providing a control fusion protein for each G protein which has an unmodified fully functional receptor (A or B) and an unmodified fully functional G-protein.

Thus, for any one G protein several constructs will be made:

(a) receptor A were the receptor is mutated will be fused to fully functional Gs, Gi and/or Gq
(b) receptor B were receptor is functional will be fused to mutated Gs, Gi and/or Gq
(c) receptor A were the receptor is functional will be fused to a mutated Gs, Gi and/or Gq
(d) receptor B were the receptor is mutated will be fused to fully functional Gs, Gi and/or Gq
(e) Fully functional fusions of Gs, Gi and Gq will be made for each of receptor A and B.

Several cell transfections may be carried out to compare the relative coupling for each. For example, to compare the coupling efficiency of Gs between the homodimer and heterodimer the following will occur:

(a) The first cell will be transfected with a combination of a) and b) above.
(b) The second cell will be transfected with a combination of c) and d) above.
(c) The third cell will be transfected with a fully functional fusion of receptor A
(d) The fourth will be transfected with a fully functional fusion of receptor B.

The response of each combination will be compared to assess potency of agonists to receptor A and B and constitutive activity. This process will be repeated for each G protein.

Jürgen Wess (Pharm. Ther. vol. 80, No. 3 1998) incorporated herein by reference provides information on the molecular basis of receptor/G-protein-coupling selectivity.

BRIEF DESCRIPTION OF THE FIGURES

Aspects and embodiments of the present invention will now be illustrated, by way of example, with reference to the accompanying figures. Further aspects and embodiments will be apparent to those skilled in the art. All documents mentioned in this text are incorporated herein by reference.

FIG. 3 shows a representation of various class A GPCRs and their associated G-protein(s), as well as residues (highlighted) in the $2^{nd}$ intracellular loop of the GPCR which are suitable for mutation.

From top to bottom: SEQ ID NOS: 1-39.

FIG. 4 shows that pairs of distinct non-functional mutants of $\alpha_{1b}$-adrenoceptor-$G_{11}\alpha$ fusion proteins reconstitute function.

A. Membranes of HEK293 cells expressing 40 (I-IV) or 80 (V) fmol of various $\alpha_{1b}$-adrenoceptor-$G_{11}\alpha$ fusion proteins were used to measure the binding of [$^{35}$S]GTPγS in the absence (open bars) or presence (filled bars) of 10 μM phenylephrine. (1) Wild type $\alpha_{1b}$-adrenoceptor-$G_{11}\alpha$, (2) $\alpha_{1b}$-adrenoceptor-Gly$^{208}$Ala$G_{11}\alpha$, (3) Leu$^{151}$Asp$\alpha_{1b}$-adrenoceptor-$G_{11}\alpha$, (4 and 5) $\alpha_{1b}$-adrenoceptor-Gly$^{208}$Ala$G_{11}\alpha$+Leu$^{151}$Asp$\alpha_{1b}$-adrenoceptor-$G_{11}\alpha$.

B. Leu$^{151}$Asp$\alpha_{1b}$-adrenoceptor-$G_{11}\alpha$ and $\alpha_{1b}$-adrenoceptor-Gly$^{208}$Ala$G_{11}\alpha$ reconstitute function only when they are co-expressed. The binding of [$^{35}$S]GTPγS in the absence (open bars) or presence (filled bars) of 10 μm phenylephrine was measured in HEK293 cell membranes in which Leu$^{151}$Asp$\alpha_{1b}$-adrenoceptor-$G_{11}\alpha$ and $\alpha_{1b}$-adrenoceptor-Gly$^{208}$Ala$G_{11}\alpha$ were co-expressed (1) or in which the two constructs were expressed in separate cells populations that were mixed prior to membrane preparation (2) or from which membranes were made separately and then mixed prior to assay (3).

Figure 5:
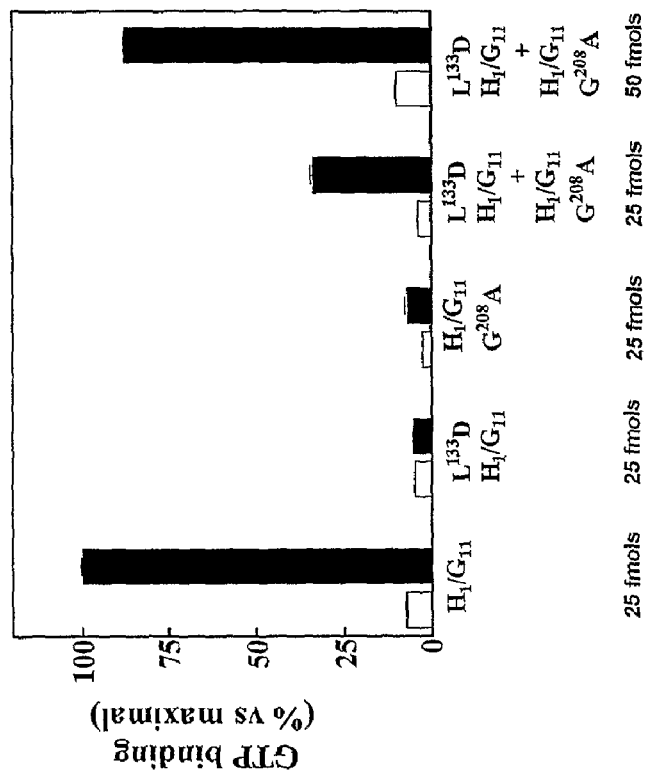

FIG. 5 shows that pairs of distinct non-functional mutants of histamine H1 receptor-$G_{11}\alpha$ fusion proteins also reconstitute function. Membranes of HEK293 cells expressing 25 (1-4) or 50 (5) fmol of various histamine H1 receptor-$G_{11}\alpha$ fusion proteins were used to measure the binding of [$^{35}$S] GTPγS in the absence (open bars) or presence (filled bars) of 1 mM histamine. (1) Wild type histamine H1 receptor-$G_{11}\alpha$, (2) histamine H1 receptor-Gly$^{208}$Ala$G_{11}\alpha$, (3) Leu$^{133}$Asp histamine H1 receptor-$G_{11}\alpha$, (4 and 5) histamine H1 receptor-Gly$^{208}$Ala$G_{11}\alpha$+Leu$^{133}$Asp histamine H1 receptor-$G_{11}\alpha$.

Figure 6:
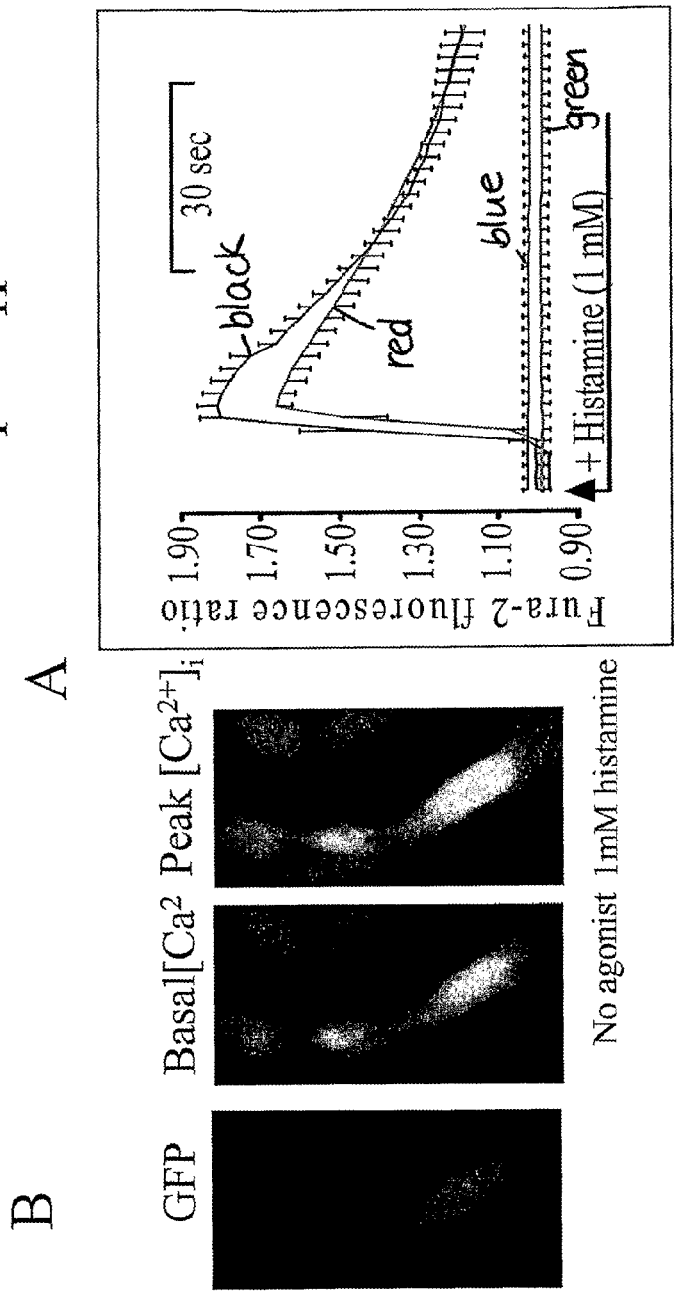

FIG. 6 shows GPCR dimerization and functional reconstitution in single cells. EF88 (mouse embryo fibroblasts derived from an animal in which the genes encoding the calcium mobilisaing G proteins $G_q\alpha$ and $G_{11}\alpha$ were inactivated) cells were transfected to express GPCR-$G_{11}\alpha$ fusion proteins and GFP and the ability of agonist ligands to elevate intracellular $Ca^{2+}$ monitored.

A. EF88 cells were transfected with GFP and histamine H1 receptor-$G_{11}\alpha$ (black, n=6), histamine H1 receptor-Gly$^{208}$Ala$G_{11}\alpha$ (blue, n=10), Leu$^{133}$Asp histamine H1 receptor-$G_{11}\alpha$ (green, n=12) and both histamine H1 receptor-Gly$^{208}$Ala$G_{11}\alpha$ and Leu$^{133}$Asp histamine H1 receptor-$G_{11}\alpha$ (red, n=8). The response of GFP positive cells to 1 mM histamine was then measured. N=the number of individual cells quantitated.

B. Only positively transfected cells respond to agonist. Cells were co-transfected with the wild type histamine H1 receptor-$G_{11}\alpha$ fusion and GFP. In the field shown only a single cell expressed GFP (left). Basal (centre) and 1 mM histamine (right) stimulated $Ca^{2+}$ was then monitored in these cells. Warmer colour represents elevated [$Ca^{2+}$]. Only an increase (warmer colour) in fluorescence was observed in the cell which expressed GFP.

Figure 7A:
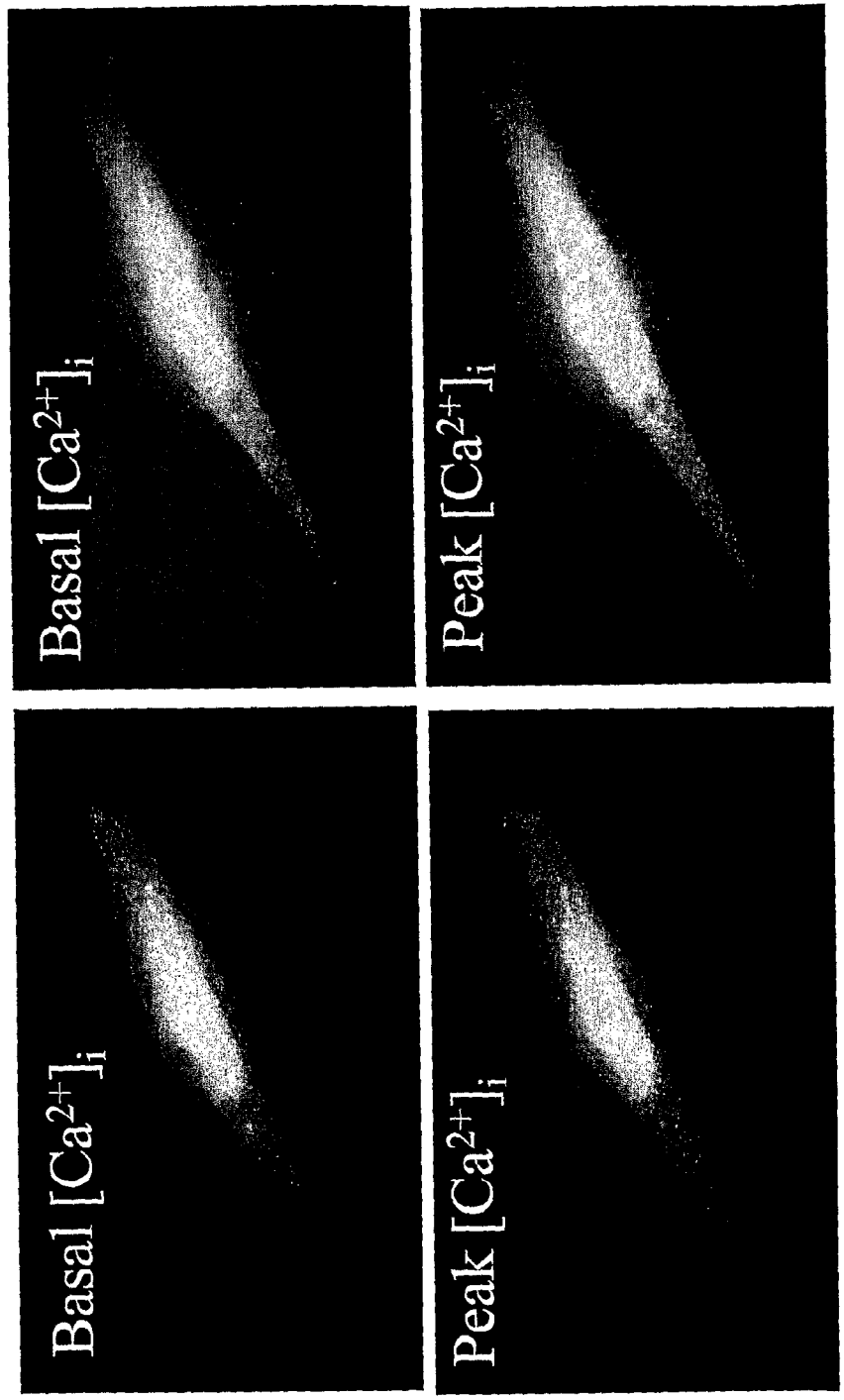

FIG. 7 shows GPCR dimerisation and functional reconstitution in single cells. Specifically, this figure shows the ability of two different GPCRs to form an oligomer, i.e. a hetero-oligomer.

A. EF88 cells were transfected to co-express a non-functional form (Leu$^{133}$Asp) of the histamine H1 receptor fused to wild type $G_{11}\alpha$ and the wild type form of $\alpha_{1b}$-adrenoceptor fused to the inactive form (Gly$^{208}$Ala) of $G_{11}\alpha$. Both of these GPCR-G protein fusions are inactive when expressed alone because each forms a non-functional homodimer. Co-transfection with GFP allowed detection of positively transfected cells. Addition of phenylephrine (10 μM) resulted in an elevation of intracellular calcium concentration but addition of histamine (1 mM) resulted in little or no change in calcium concentration. This can only reflect that the occupation of the $\alpha_{1b}$-adrenoceptor by the agonist phenylephrine results in activation of the wild type $G_{11}\alpha$ that is physically linked to the inactive histamine H1 receptor and reflects the presence of a functional $\alpha_{1b}$-adrenoceptor-histamine H1 receptor heterodimer.

B. In an analogous fashion EF88 cells were also transfected to co-express a non-functional form (Leu$^{151}$ASP) of the $\alpha_{1b}$-adrenoceptor fused to the wild type $G_{11}\alpha$ and the wild type form of the histamine H1 receptor fused to the inactive form (Gly$^{208}$Ala) of $G_{11}\alpha$. In this format addition of phenylephrine (10 μM) resulted in little or no change in calcium concentration, whilst addition of histamine (1 mM) resulted in elevation of intracellular calcium.

Figure 8:
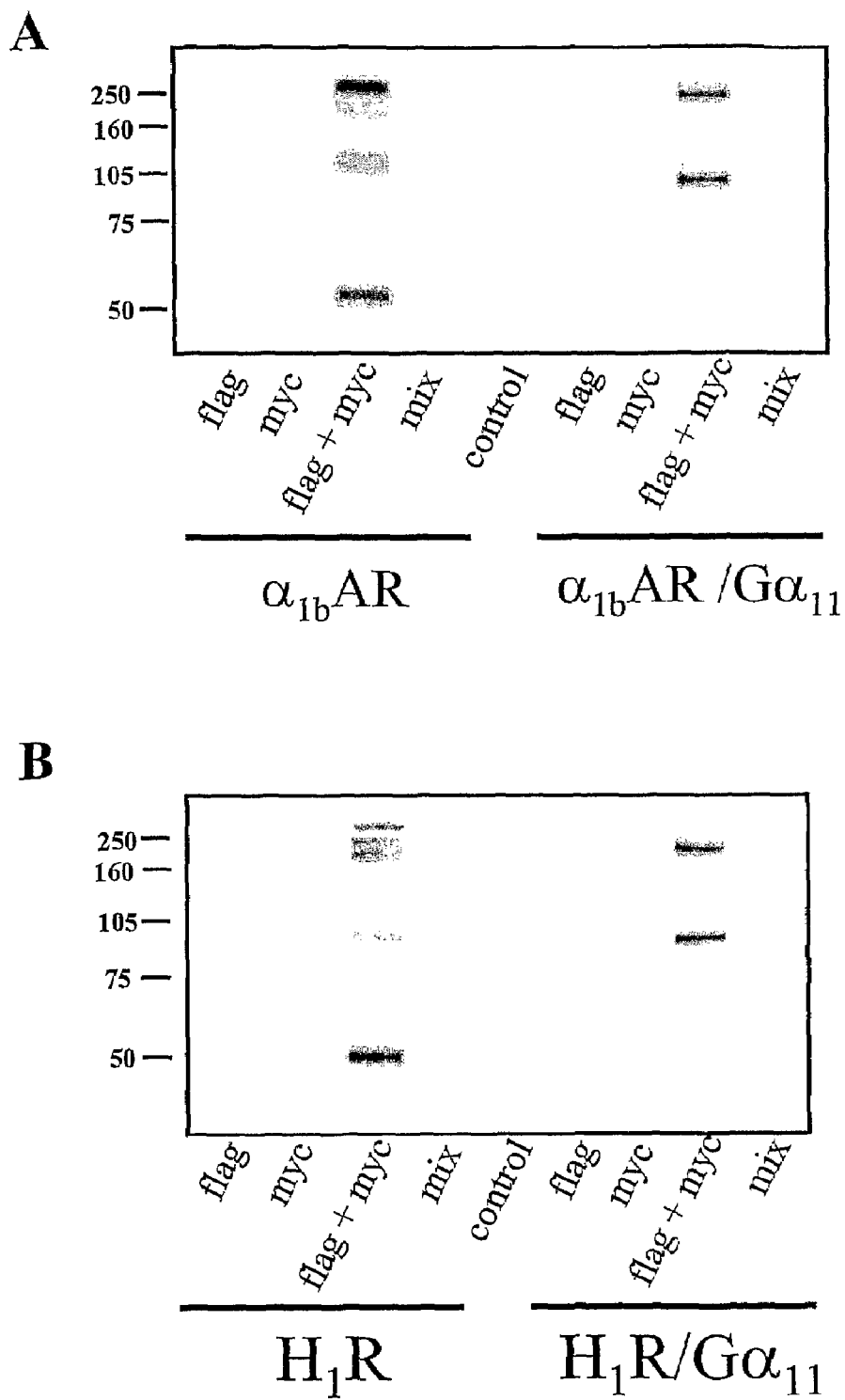

FIG. 8 shows co-immunoprecipitation of differentially epitope tagged forms of both GPCRs and GPCR-G protein fusions and demonstrates that addition of the G protein to the C-terminal tail of a GPCR does not prevent dimerisation.

A. $\alpha_{1b}$-adrenoceptor constructs.

B. histamine H1 receptor constructs. HEK293 cells were mock transfected (control) or transfected to express either FLAG, c-myc or a combination (FLAG+myc) of both epitope tagged forms of the isolated GPCRs or GPCR-G protein fusions. Cells expressing either FLAG or c-myc tagged forms were also mixed (mix). Samples were immunoprecipitated with anti-FLAG antibody, these precipitates resolved by SDS-PAGE and immunoblotted with anti c-myc antibodies.

Figure 9:
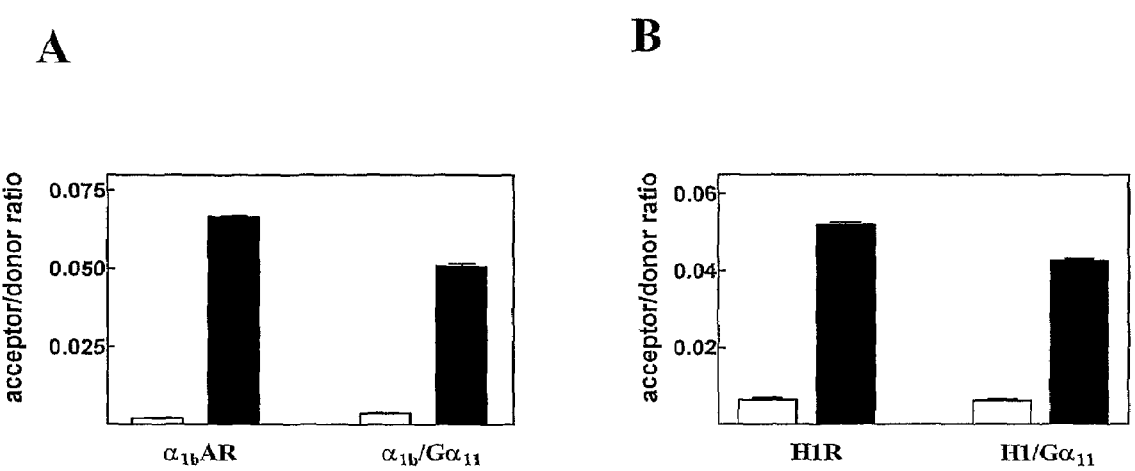

FIG. 9 shows that trFRET demonstrates cell surface oligomers of both GPCRs and GPCR-G protein fusions.

A. $\alpha_{1b}$-adrenoceptor constructs.

B. histamine H1 receptor constructs. HEK293 cells were transfected individually (mix) to express either FLAG or c-myc tagged forms of the isolated GPCRs or GPCR-G protein fusions. These cells were then mixed together. HEK293 cells were also transfected to co-express FLAG and c-myc epitope tagged forms of the isolated GPCRs or GPCR-G protein fusions (cotransf). Cells were then exposed to Eu3+-labelled anti-c-myc antibodies and allophycocyanin labelled anti-FLAG antibodies (see methods). Energy transfer was then monitored as described in McVey et al. (2001). Energy transfer is consistent with the FLAG and c-myc tagged polypeptides forming physical complexes (dimers). When expressed in different cells the distance between the FLAG and c-myc tagged polypeptides is too great to allow effective energy transfer and when in different cells they cannot interact. These experiments thus act as a negative control.

Figure 10:
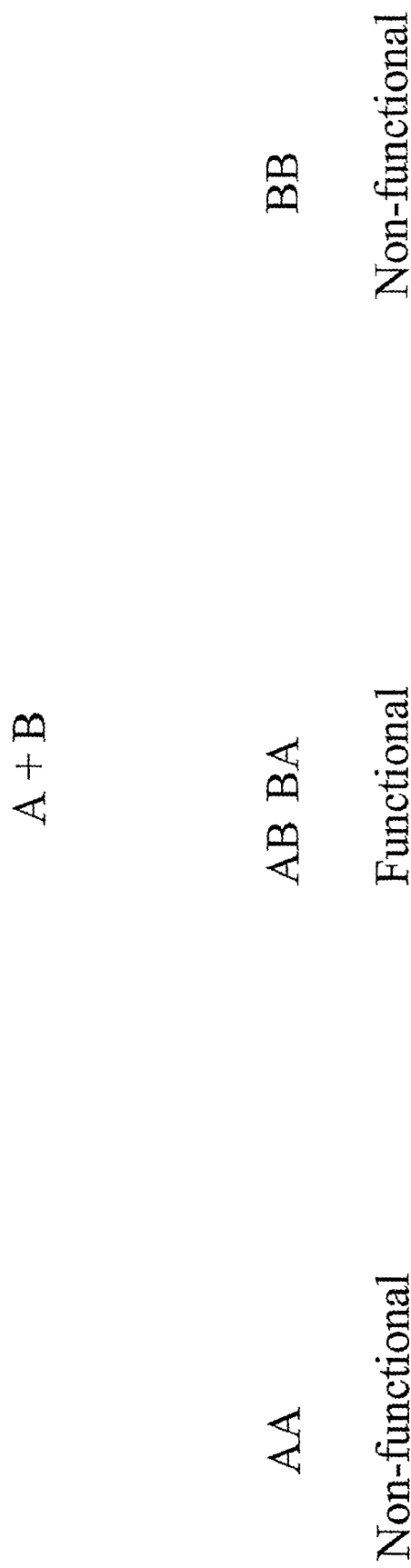

FIG. 10 shows that co-expression of pairs of non-functional GPCR-G protein fusions should generate 50% of active dimers. If two distinct GPCRs or GPCR-G protein fusion proteins are co-expressed in a single cell and the affinity of interaction of A with A is the same between A and B then stochastically it must be expected that AA, AB, BA and BB will be present in equimolar amounts. As demonstrated in FIG. 2, the methodology developed by the inventors ensures that AA and BB do not respond functionally to addition of ligands for either A or B However, both AB and BA are potentially functional on addition of ligands for either A or B (see FIG. 7C). Thus only 50% of the dimers that form following co-expression of A and B are expected to be functional and these are the combination of each of the differently mutated fusion proteins, e.g. AB or BA.

FIG. 11 shows the $\alpha_{1b}$-adrenoceptor and the histamine H1 receptor can form hetero-dimeric complexes.

A. A FLAG-tagged form of the histamine H1 receptor (flag H1) and a c-myc-tagged form of the $\alpha_{1b}$-adrenoceptor (myc $\alpha_{1b}$) were expressed either individually or together (flag+ myc) in HEK293 cells. Cells expressing the two constructs individually were also mixed prior to analysis. Samples were immunoprecipitated with anti-FLAG and after SDS-PAGE and transfer, immunoblotted with anti-c-myc-antibodies.

B. Cells either co-expressing FLAG H1 and c-myc $\alpha_{1b}$ (filled bars) or separate populations of cells expressing either of the two constructs that were then mixed were treated with a combination of Eu$^{3+}$-labelled anti-c-myc and APC-labelled anti-FLAG antibodies were added and tr-FRET measured.

Figure 12:
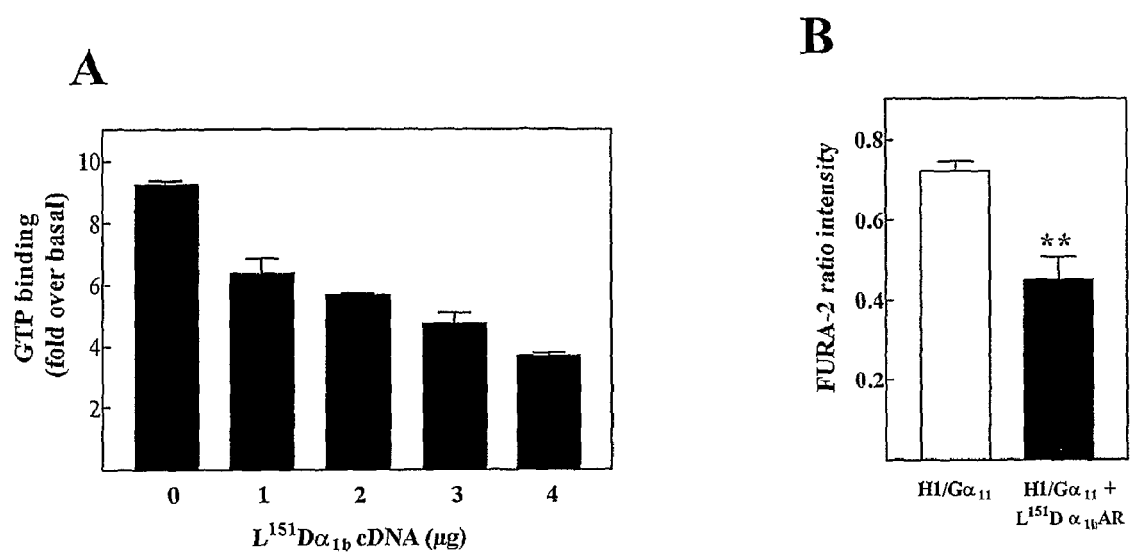

FIG. 12 shows co-expression of an inactive form of the $\alpha_{1b}$-adrenoceptor suppresses signalling by a histamine H1 receptor-$G_{11}\alpha$ fusion protein.

HEK293 cells were transfected to express the histamine H1 receptor-$G_{11}\alpha$ fusion protein and with increasing amounts of cDNA encoding the isolated, inactive Leu$^{151}$Asp $\alpha_{1b}$-adrenoceptor. (A) Membranes from these cells were used to measure expression of the histamine H1 receptor-$G_{11}\alpha$ fusion protein and amounts containing 25 fmol of specific [$^3$H]mepyramine binding sites were used to measure basal and 1 mM histamine-stimulated [$^{35}$S]GTPγS binding. (B) EF88 cells were transfected to express the histamine H1 receptor-$G_{11}\alpha$ fusion protein (1) or to co-express this with Leu$^{151}$Asp $\alpha_{1b}$-adrenoceptor. The ability of 1 mM histamine to elevate cellular [Ca$^{2+}$]i was then assessed. Data represent means+/−S.E.M. n=6.

Figure 13:
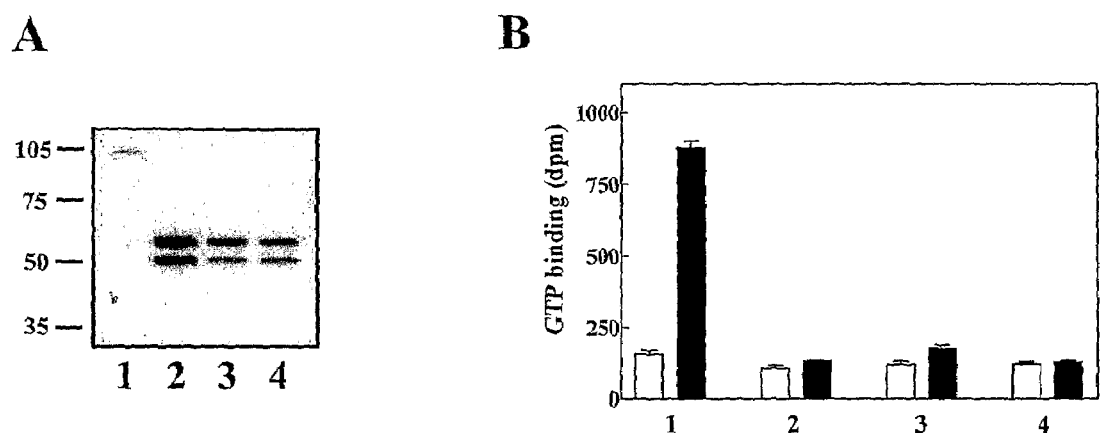

FIG. 13 shows provision of excess membrane targeted $G_{11}\alpha$ does not account for the reconstitution of function in cells expressing pairs of non-functional mutants. HEK293 cells were transfected to express the c-myc-tagged $\alpha_{1b}$-adrenoceptor-$G_{11}\alpha$ fusion protein (1), $G_{11}\alpha$ linked to the C-terminus of a c-myc-tagged form of the N-terminal and first transmembrane region of the $\alpha_{1b}$-adrenoceptor (2), both the $\alpha_{1b}$-adrenoceptor and the c-myc-Nt-TM1$\alpha_{1b}$-$G_{11}\alpha$ construct (3) or c-myc-Nt-TM1$\alpha_{1b}$-$G_{11}\alpha$ and the $\alpha_{1b}$-adrenoceptor-Gly$^{208}$Ala$G_{11}\alpha$ fusion protein (4). (A) Membrane samples were resolved by SDS-PAGE and immunoblotted with anti-c-myc antibodies. (B) Basal (open bars) and 10 μM phenylephrine stimulation (filled bars) of binding of [$^{35}$S] GTPγS recovered in anti-c-myc immunoprecipitates.

DETAILED DESCRIPTION

Figure 1:
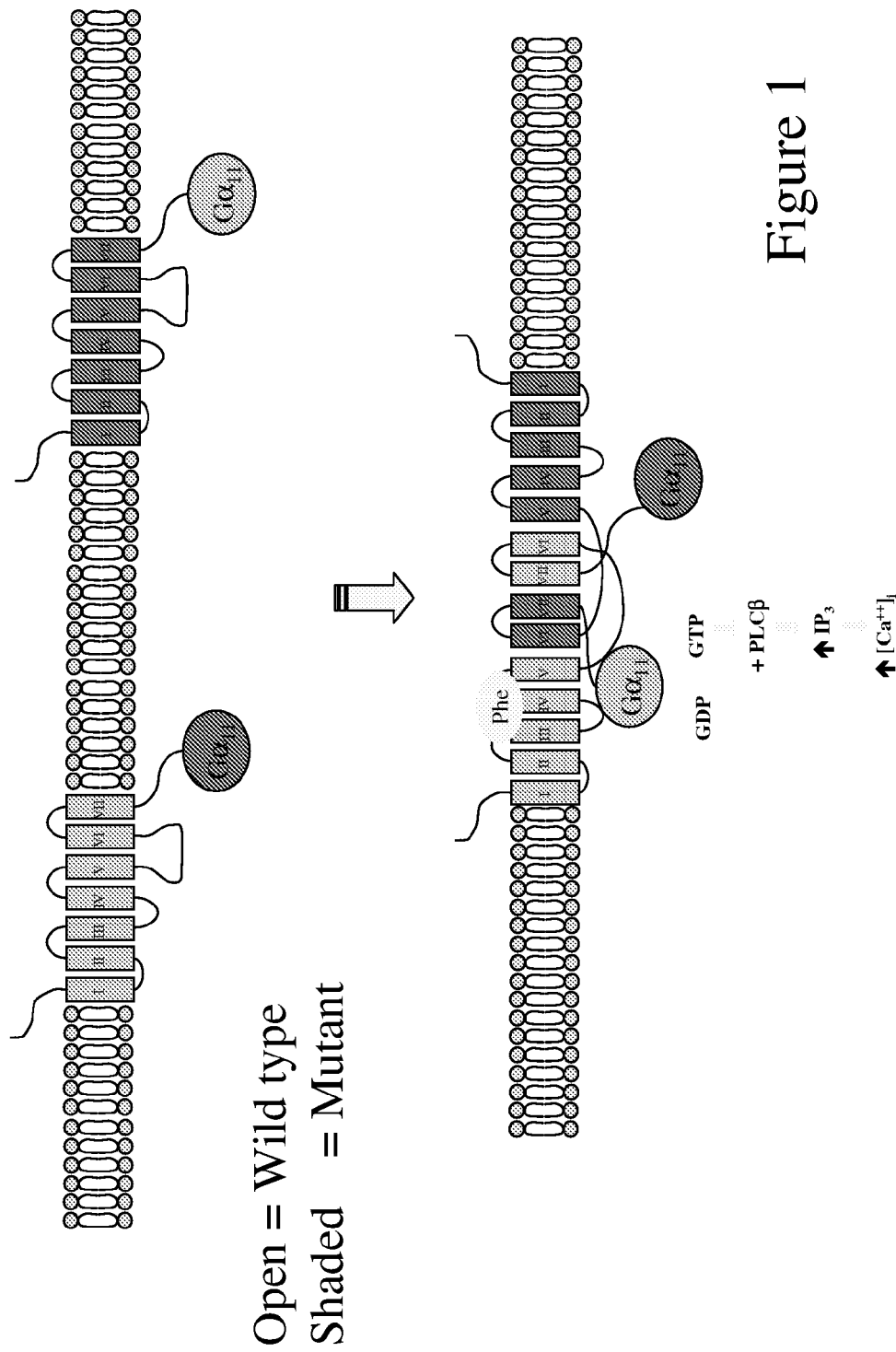
FIG. 1 shows a schematic diagram of how it is envisaged reconstitution of function by pairs of mutants occurs. This Figure exemplifies the use of GPCRs fused to a G protein that typically results in the elevation of intracellular calcium concentrations.

FIG. 1 shows a representation of how the inventor envisages reconstitution of function by pairs of mutants can occur, thus forming a functional oligomer. As can be seen the functional oligomer is constituted of a first fusion protein (a) comprising a native GPCR and a mutant G-protein and a second fusion protein (b) comprising a mutant GPCR and a native G-protein. When these two fusion proteins combine functional activation of the GPCR signalling cascade occurs by agonist ligand binding to the native GPCR of the first fusion protein and functional coupling and signalling through the G-protein of the second fusion protein.

Figure 2:
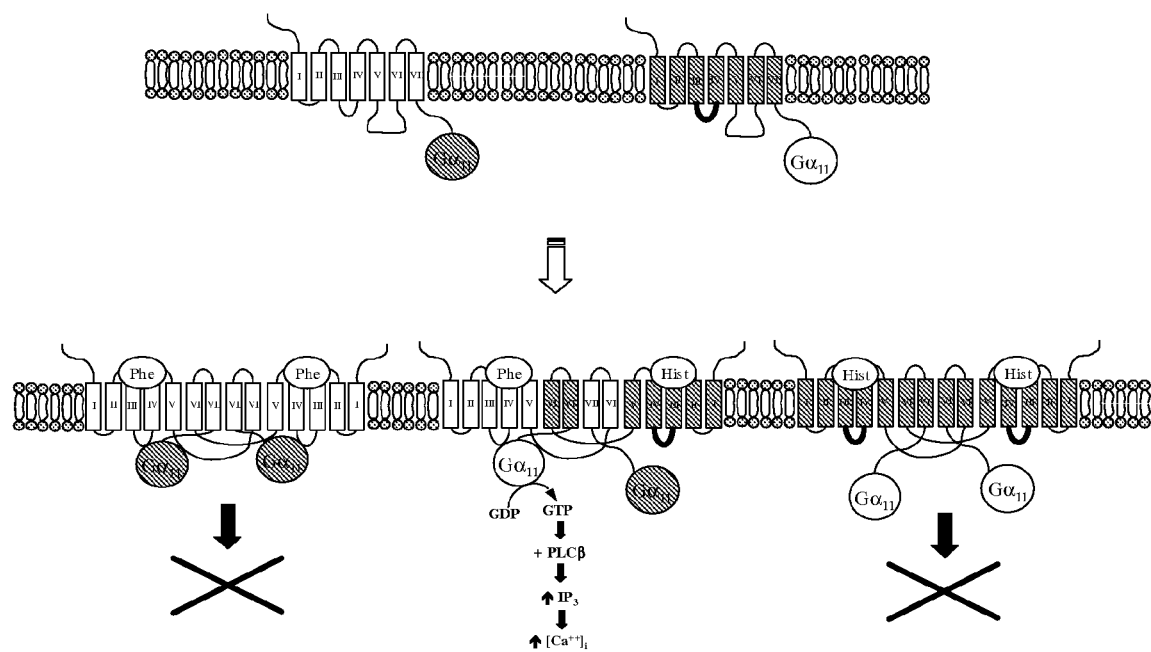
FIG. 2 shows a schematic diagram of how only a oligomer (in this case a dimer) GPCR/G-protein fusion is functional and homomeric forms are non-functional.

FIG. 2 shows how it is envisaged that non-functional homodimers are formed. The non-functional homodimers comprise either 2 native GPCRs and two mutant G-proteins (a), or two mutant GPCRs and two native G-proteins (b). In either case, the 2 forms of homodimer cannot lead to functional signalling when an appropriate ligand binds to the GPCR.

The GPCR and Associated G-Protein

The GPCR and G-protein may be any suitable GPCR/G-protein combination. A non-exclusive list of GPCRs may be found at the world wide website of gpcr.org. Preferably the GPCRs and G-proteins are of mammalian origin, more preferably human origin. Typical G protein coupled receptors are for example dopamine receptors, muscarinic cholinergic receptors, α-adrenergic receptors, β-adrenergic receptors, opiate receptors, cannabinoid receptors, serotonin receptors, somatostatin receptors, adeno sine receptors, endothelium receptors, chemokine receptors, melanocortin receptors, neuropeptide Y (NPY) receptors, GnRH receptors, GHRH receptors, TSH receptors, LH receptors, and FSH receptors. Other GPCRs which may be used in accordance with the present invention are described (along with their ligands) in Trends in Pharmacological Sciences: Ion Channel Nomenclature Supplement compiled by S. P. H. Alexander & J. A. Peters, 11$^{th}$ Edition, Current Trends, London, UK 2000, and The RBI Handbook of Receptor Classification and Signal Transduction, K. J. Watling, J. W. Kebabian, J. L. Neumeyer, eds. Research Biomedicals International, Natick, Mass., 1995. Vassilatis et al. PNAS, April 2003, vol. 100, 4903-4908. These references are incorporated herein by reference.

It is preferable for all aspects of the present invention that where the first and second GPCR are different, they are endogenously co-expressed by at least one cell type.

GPCRs are presently grouped into 3 main classes—A, B & C. Class A are also called the Rhodopsin-like or rhodopsin family receptors, Class B are the secretin like receptors, Class C the metabotropic receptors. Although all are GPCRs the three families have no sequence similarities and appear to have been an example of convergent evolution. Examples in Class A include receptors for catecholamines such as adrenaline, histamine, dopamine and serotonin as well as receptors for (neuro) peptides including the opioid peptides, neurokinins, orexins, etc. The olfactory receptors are also part of this group. The Class B receptors total around 65 and the Class C receptors about 18, these include the GABAb receptor, the calcium sensing receptor and a family of seven metabotropic glutamate receptors. There are other families of proteins which have yet to be conclusively classed as GPCRs. These include the "frizzled" receptor family and the "Methuselah" receptors.

The G-protein may be any G-protein able to associate/couple with a GPCR. The G-protein preferably has the ability to modulate an intracellular level of $Ca^{2+}$, cAMP, cGMP, inositol 1, 4, 5 triphosphate, diacylglycerol, protein kinase C activity, or MAP kinase activity.

For example, activation of Gi, Go, or Gz leads to a reduction of the intracellular level of cAMP. Activation of Gq, G11, G15 or G16 leads to an increase in the intracellular level of inositol 1, 4, 5 triphosphate and $Ca^{2+}$.

The G-protein may also be selected from the group consisting of Gi, Go, Gz, G11, G12, G13, G15 G16, Gs and Gq.

In addition to those identified herein, it is well within the expertise of the skilled reader to identify further GPCRs based on sequence information. All GPCRs possess seven highly hydrophobic regions that are long enough (20-25 amino acids) to cross the plasma membrane. Within these some amino acids are substantially always there. For example, in Class A GPCRs there is virtually always a sequence Aspartic acid-Arginine-Tyrosine or something very similar (this is called the DRY domain because of the single letter amino acid code for Aspartic acid (D)-Arginine (R)-Tyrosine (Y). The skilled addressee can also conduct searching with mathematical algorithms such as the "Hidden Markov" method to identify further GPCRs.

Conveniently, the GPCR may be a class A GPCR, examples of which, together with their associated G-protein(s) are shown in FIG. 3.

Modification of GPCR and G-Protein

FIG. 3 also shows highly conserved residues in the 2$^{nd}$ intracellular loop of the GPCR which are, for example, suitable for mutation and rendering the GPCR substantially non-functional. Mutation of these residues has been shown by the inventor to be particularly efficacious in rendering a GPCR inactive but still capable of binding ligands. Moreover, as the hydrophobic residues are highly conserved, it is envisaged that all class A GPCR can be mutated in this manner to render them inactive. Typically the residue is a hydrophobic one, which may be mutated to an acidic residue by for example site-directed mutagenesis techniques known in the art. However, any other mutation which renders the GPCR functionally inactive or substantially functionally inactive may be carried out and their activities/lack of activity tested using the assays described herein-after in relation to assaying heterodimer activity. That is, a functional assay for a native GPCR may be carried out on a mutagenised GPCR in order to ascertain what degree of activity remains after mutagenisation. If a first round of mutagenesis is not sufficient to render a GPCR inactive, a further round of mutagenesis may be carried out and activity tested thereafter.

It is also possible to conduct random mutagenesis or applied molecular evolution and then test the activity of the mutants. Moreover crystal structures of G proteins are known and important residues identified therefrom, so that targeted mutagenesis can be carried out.

A publicly available program (TMHMM) found at the world wide web site of the Center for Biological Sequence Analysis may be used by the skilled person to identify transmembrane domains with the GPCR structure. This allows site directed mutagenesis to be carried out in order to determine mutants which render the GPCR inactive but still able to bind ligand. The 2nd intracellular loop (IC2) would be defined as the polypeptide segment between transmembrane (TM)3 and TM4. This site would at least provide guidance with respect to identifying the neighbourhood of a GPCR amino acid sequence that one would want to align with the IC2 sequences in FIG. 3 for the purpose of making an analogous mutation(s).

The membrane GPCRs mentioned herein are typically modified by the fusion of an associated G-protein to the receptor. Typically nucleic acid encoding the G-protein may be fused in-frame to the 3' end, of a gene encoding the particular GPCR from which the stop codon has been eliminated. In this manner, on expression of the nucleic acid, the reporter protein is functionally expressed and fused to the C-terminal end of the GPCR. Modification of the receptor is such that the functionality of the membrane receptor remains substantially unaffected by fusion of the G-protein to the receptor.

The mutation which can be carried out to the G-protein, may be any suitable mutation which renders the G-protein non-functional (i.e. unable to functionally bind GTP and initiate the GPCR signalling cascade). Again, this can easily be tested by the skilled addressee using the assays described herein. One suitable mutation which may be made is mutation of the glycine at position 208 of $G_{11}\alpha$ to, for example alanine. All G-proteins possess the glycine at position 208, or equivalent site/residue and so an equivalent mutation is envisaged to render other G-proteins inactivate. Other suitable mutations can easily be identified as those which effect the sequences that allow proteins to bind and hydrolyse GTP. To date G-protein sequences have been observed as being highly conserved through evolution and the sequences identified as being involved in allowing proteins to bind and hydrolyse GTP are highly conserved.

It is therefore a relatively straightforward task to be able to couple any receptor (native or mutant) to an appropriate G-protein (native or mutant).

Constitutively Active GPCRs and Functional Genomics

Perhaps the most challenging step in drug development today relates to target validation. The large public, and private, human genome sequencing efforts which have come to fruition in recent years have provided unprecedented numbers of gene targets for pharmaceutical development. Deciphering the functionality and, most importantly, potential therapeutic relevance of these gene targets is of high priority as the basis for the development of next-generation therapeutics. This challenge is of no greater magnitude than within the GPCR gene family where large numbers of novel genes have been identified. Having identified GPCRs exhibiting high or selective expression within tissues of interest it is possible to further refine the analysis to the cellular level. This may involve using both RNA probes and antibodies to map the cellular populations within tissues which express any GPCRs of interest.

For orphan GPCRs with no identified ligand, constitutively active forms of the receptor may then be employed as a tool to further investigate their functional roles. Such an approach, in essence, simulates the effect of ligand stimulation on the target GPCR. For example, orphan GPCRs have been identified which are selectively expressed within pancreatic B cells as a means to identify potential targets to regulate insulin secretion. Examination of the constitutively active form of one such receptor, "islet receptor 1", in in vitro systems confirms that the receptor couples to the appropriate cellular signaling molecules (adenylate cyclase) to regulate insulin release. Furthermore, utilization of this constitutively active receptor in an insulin producing cell line confirms that the active form of the receptor enhances glucose-sensitive insulin release. These data provide highly suggestive information supporting the development of "islet 1" GPCR agonists as a means to regulate insulin release.

In order to examine GPCR expression comprehensively, an oligonucleotide GPCR chip has been synthesised by Arena Pharmaceuticals Inc., 6166 Nancy Ridge Drive, San Diego, Calif. 92121, USA., containing all available human GPCR sequences, as well as markers for cellular function and disease state. This approach allows rapid identification of gene expression profiles for GPCRs across a wide variety of human tissues on a macro scale. Cluster analysis can also be applied to identify tissue-specific patterns of gene expression which may indicate functional roles. Assessment of the tissue distribution of GPCRs and related signaling molecules may therefore clarify the complexity of the molecular mechanisms by which receptor signaling transduce extracellular stimuli. The sequencing of the human genome has brought new avenues by which global approaches can be undertaken to investigate the breadth of GPCR signaling. It is now estimated that the GPCR superfamily consists of 600-1000 receptors. The advent of microarray technology allows for a large sampling of the receptor family to be performed. This technology permits one to monitor the message levels of thousands of genes simultaneously in a given sample. Evaluation of the transcriptional levels for these genes across a large panel of tissues would thus provide a global view of GPCR signaling in the human body.

Cells Suitable for Expression of Modified GPCR and G-Protein

A variety of cells may be used to express nucleic acid constructs encoding the fusion proteins of the present invention. All cells that can be transfected to express the modified GPCRs are considered to be within the scope of the invention. Examples of such cells include neonatal cells, endocrine cells, tumour cells, acinar cells, islet cells, immune cells, neuroendocrine cells, neuronal cells, and pituitary cells. It is also well within the capabilities of the skilled person to determine other cell lines which are able to express the modified GPCRs in accordance with the invention, e.g. CHO (Chinese hamster ovary) cells (CHO-K1) and HEK (human embryonic kidney) cells.

In carrying out the assays of the present invention, it may be preferable to use cell lines which do not express any endogenous GPCRs to high levels. CHO-K1 is an example of such a cell line.

Certain cells may be chosen to express the GPCR oligomers of the present invention owing to their ability to react to GPCR signalling cascade. For example, in assays for determining a ligand for a GPCR oligomer, it may be convenient to express the GPCR in a cell which has a detectable change in characteristic upon receptor activation, e.g. pigment cells. U.S. Pat. No. 5,462,856 (incorporated herein by reference) describes methods of developing rapid and sensitive bioassays for evaluating new agonists and antagonists for GPCRs using pigment cell lines. Assays for determining GPCR activity are discussed in more detail below. Accordingly, pigment cells which may be transfected with nucleic acid constructs according to the present invention include chromatophores, melanophores or melanocytes, xanthophores, erythrophores, leukophores and iridophores. Such cells may conveniently be obtained from lower animals such as Reptilia, e.g. *Anolis* sp: Amphibia, e.g., *Xenopus laevis*; Pieces, e.g., *Zacco ternmincki*; Crustacia, e.g., *Uca pugilator*; Echinodermata, e.g., *Diadema antillarum* and Cinidaria, e.g., *Nanomsa cara*. Particularly preferred pigment cells for use in the present invention are cultured melanophores from the *Xenopus laevis* (Pigment Cell 1985), ed. Bagnara et al., University of Tokyo Press, pages 219-227) and Lerner et al. (1988) *P.N.A.S. USA*, 85: 261-264.

Using nucleic acid constructs to transfect a cell is well within the capabilities of the person skilled in the art Standard methods include lipofectamine, calcium phosphate precipitation, electroporation, gene guns, liposomes and viral vectors.

An expression vector e.g. plasmids, viral vector etc. is a replicable DNA construct in which the nucleic acid is operably linked to suitable control sequences capable of effecting the expression of the membrane receptor/reporter fusion in the particular cell. Typically control sequences may include a transcriptional promoter, an optional operator sequence to control transcription, a sequence encoding suitable mRNA ribosomal binding sites, and sequences which control the termination of transcription and/or translation. Typically expression vectors may include for example plasmids, bacteriophages or viruses and such vectors may integrate into the host's genome or replicate autonomously in the particular cell.

A variety of expression vectors are available to the skilled person. A preferred vector is pCMV which is deposited at ATCC under deposit number ATCC #203351.

In order for the particular cell to express the mutant GPCR/G-protein fusion proteins the cell must be transformed by the appropriate expression vector. "Transformation", as used herein, refers to the introduction of a heterologous polynucleotide fragment into a host cell, irrespective of the method used, for example direct uptake, transfection or transduction.

The present invention therefore also relates to cells which have been transformed by nucleic acid constructs comprising mutant GPCR/G-protein fusions of the present invention and which express the mutant GPCR/G-protein fusion proteins. In the methods of the present invention, the cells may be lysed prior to use, such that only the cell membranes, in which the GPCR is located, may be used.

Assays for Determining GPCR Activity

Having co-transfected a cell with nucleic acid constructs encoding the modified GPCRs, it may then be evaluated for binding of at least one ligand specific for at least the functional (second) GPCR. The functional activity of a GPCR oligomer in accordance with the present invention may be determine by a number of standard and well known techniques. GPCRs are known to affect adenylyl cyclase activity, to modulate the conductance of voltage-gated calcium channels, to modulate potassium channels, to activate the MAP kinase pathway, to activate the phospholipase C (PLC)—$IP_3$ pathway, to activate phosphotyrosine phosphatase, to stimulate mitogenesis, to stimulate exocytosis, to stimulate cytostasis, to stimulate chemotaxis and to induce apoptosis. These activities may be measured by the skilled person using routine and standard methods. The functional activity may also be determined using these techniques in assays for determining a ligand of the GPCR (see below).

Observing the effect said compound has on the functioning of the GPCR heterodimer may be carried out by assaying for a level of a down-stream component of said GPCR signalling cascade. One convenient component to detect is a level/ change in level of calcium. Typically as calcium ions. As an alternative to calcium detection, it is also possible to utilise analogues of GTP, which bind to the active G protein, as detection agents and also reporter gene assays known to those skilled in the art.

The level of cytosolic calcium within the normal and abnormal cells may be detected by methods known to the skilled addressee that monitor cytosolic calcium levels. Indicator dyes may be used, for example fluorescent probes (such as fura-2, fluo-3 or -4, indo-1, quin-2) show a spectral response upon binding calcium and it is then possible to detect changes in intracellular free calcium concentrations using for example fluorescence microscopy, flow cytometry and fluorescence spectroscopy. Most of the above fluorescent indicators are variations of the nonfluorescent calcium chelators EGTA and BAPTA. Other examples are obtainable from, for example, Molecular Probes, Oregon, USA.

Additionally, the present methods are particularly suited to the development of high-throughput screens where detection may be carried out using for example a CCD camera, a luminometer, or any other suitable light detection system. In this manner, cells/cell membranes may be provided for example in multi-well plates to which test substances and reagents necessary for the detection of intracellular calcium may be added. Moreover, commercially available instruments such as "FLIPR-flumetric imaging based plate reader" (Molecular Devices Corp, Sunnyvale, Calif., USA) may be used. New fluorescent indicators for calcium called "chameleons" may also be used and are genetically encoded without cofactors and are targetable to specific intracellular locations. These so-called "chameleons" consist of tandem fusions of a blue- or cyan-emitting mutant of the green fluorescent protein (GFP), calmodulin, the calmodulin-binding peptide M13, and an enhanced green- or yellow-emitting GFP. Binding of calcium makes calmodulin wrap around to M13 domain, increasing (Miyawaki et al 1997) or decreasing (Romoser et al 1997) the fluorescence resonance energy transfer between flanking GFPs.

Another method for intracellular calcium concentration measurement is the use of cell lines overexpressing a GPCR and apoaequorin, such as described by Sheu et al. (1993). In this system, cells expressing apoaequorin are incubated with coelenterazine, which is the co-factor of aequorin. During this incubation, coelenterazine enters the cell and conjugates with apoaequorin to form aequorin, which is the active form of the enzyme. Upon incubation of the cells with an agonist of the GPCR, intracellular calcium concentration increases. This increase leads to the activation of the catalytic activity of aequorin, which oxidises coelenterazine and yields apoaequorin, coelenteramide, $CO_2$ and light. Once the photon has been emitted, the complex must dissociate and apoaequorin must recombine with a new coelenterazine molecule to be able to emit light again. Thus, in this system, measurement of light emission following agonist addition reflects its ability to activate the GPCR and thus to increase intracellular calcium concentration.

Other suitable detection mechanisms include detection of other second messengers apart from $CA^{2+}$ e.g. cAMP levels, cGMP levels, inositol 1, 4, 5 triphosphate levels, diacylglycerol levels, protein kinase C activity or MAP kinase activity). It is also possible to use reporter genes because activation of GPCRs generally results in changes in gene expression over time (this can be done with reporters coupled to promoter elements that respond to changes in cAMP levels or activation of kinases). A further method utilises melanocytes as described for example in U.S. Pat. No. 5,462,856 (incorporated herein by reference) and U.S. Pat. No. 6,051,386 (incorporated herein by reference), which describe methods in which signals generated by functional activation of a GPCR alter the aggregation state of pigment in the cells and the cell either appear more or less opaque due to the pigmentation, which is easily detected by, for example, colourimetric means. The alteration of the aggregation state may result in increased aggregation or conversely a decrease in aggregation (dispersion).

Reporter Assays

The signaling from GPCR oligomers can also be assessed using a variety of reporter systems. To measure changes in intracellular cAMP levels a reporter construct driven by a promoter containing cyclic AMP response elements (CRE) would be preferable. To measure responses driven from a Gq pathway that lead to activation of protein kinase C a PKC-sensitive reporter system would be preferable that contained AP1 sites in its promoter sequence. Other reporters sensitive to MAP kinase activation and reporters containing serum response elements (SREs) could also be use to measure responses from the GPCR oligomers. The reporter molecules themselves can range and examples of these include, luciferase, beta-galactosidase, beta-lactamase, green fluorescent protein, yellow fluorescent protein and others.

Determination of Ligand Binding

The present invention is particularly suited for determining new ligands which bind to a GPCR as a result of oligomerization. Naturally occurring and synthetic ligands well known to the skilled person may be tested. Suitable test ligands may come from combinatorial libraries, peptide and peptide mimetics, defined chemical entities, oligonucleotides, and natural product libraries which may be screened for activity. In one possible approach the candidate substances may for example be used in an initial screen in batches, for example 10 substances per reaction, and the substances of those batches which show an effect tested individually.

Typically the assay may be used to screen compounds for their effect on particular membrane GPCRs. Compounds identified as having an effect on a particular membrane receptor may be useful, for example, in modulating the activity of wild type and/or mutant membrane receptors; may be used in elaborating the biological function of particular membrane receptors; and/or may be used in screens for identifying compounds that disrupt normal membrane receptor interactions, or can in themselves disrupt such interactions.

The assay is particularly suited for the detection of compounds which serve as inverse agonists, antagonists or agonists of the membrane receptor. The term inverse agonist is understood to mean a compound which when it binds to a receptor, selectively stabilises and thus enriches the proportion of a receptor in a conformation or conformations incapable of inducing a downstream signal. Agonist is understood to mean a compound which when it binds to a receptor selectively stabilises and thus enriches the proportion of the receptor in a conformation or conformations capable of inducing a downstream signal. Antagonist is understood to mean a compound which when it binds to a receptor has no selective ability to enrich either active or inactive conformations and thus does not alter the equilibrium between them.

The present invention also therefore relates to inverse agonists, antagonists or agonists of receptor proteins identified using the assays according to the present invention and to the use of such agonists, antagonists or agonists in studying dimer or oligomer GPCR function, or therapy.

The following provides specific examples for working the present invention, and outlines the work carried out by the inventor resulting in the present invention.

Materials and Methods

A fibroblast cell line (EF88) (Gohla et al, 1999) derived from a combined $G\alpha_q/G\alpha_{11}$ double knockout mouse (Offermans, et al, 1998) was the gift of Dr. M. I. Simon, California Institute of Technology, Pasadena Calif. All materials for tissue culture were supplied by Life Technologies Inc. (Paisley, Strathclyde, UK). [$^3$H]prazosin (80 Ci/mmol), [$^3$H]mepyramine (30 Ci/mmol) and [$^{35}$S]GTPγS (1250 Ci/mmol) were from NEN/Perkin Elmer. Oligonucleotides were purchased from Cruachem (Glasgow, Strathclyde, UK). Reagents for time-resolved fluorescence resonance energy transfer were from Wallac. Receptor ligands were purchased from RBI (Gillingham, Kent, U.K. Production and characterization of the anti-$G_q/G_{11}$ antiserum CQ was described by (Mitchell et al, 1991; Mitchell et al, 1993). Widespread distribution of $G_q/G_{11}\alpha$ detected immunologically by an anti-peptide antiserum directed against the predicted C-terminal decapeptide. FEBS Lett. 287, 171-174.

All other chemicals were from Sigma (Poole, Dorset, U.K.) and were of the highest grade available.

Construction of Fusion Proteins

Production and subcloning of wild type and mutated $\alpha_{1b}$-adrenoceptor-G $\alpha_{11}$ fusion proteins was performed as described in (Carrillo, et al., 2002). Production and subcloning of the human histamine $H_1$ receptor-$G_{11}\alpha$ fusion proteins was performed in two separate stages. In the first step, using the amino-terminal primer 5'-GATACTGGGCTATC-CAAGCTTATGAGCCTCCCCAATTCCTC-3' (SEQ ID NO:40), a HindIII restriction site (underlined) was introduced by PCR upstream of the coding sequence of the human histamine $H_1$ receptor. Using a carboxyl-terminal primer 5'-AAGGAAAAAAGCGGCCGCTGGAGC-GAATATGCAGAATTCTCT-3' (SEQ ID NO:41) a three amino acid spacer (Ser-Gly-Arg) and a NotI restriction site were introduced immediately upstream of the stop codon. Similarly, the mouse $G_{11}\alpha$ sequence was amplified by PCR using the amino-terminal primer 5'-AAGGAAAAAAGCG-GCCGCATGACTCTGGAGTCCATGATGGC-3' (SEQ ID NO:42) and the carboxyl-terminal primer 5'-ATGAAAC-CGCTCGAGTCACACCAGGTTGTACTCCTTCAG-3' (SEQ ID NO:43). This introduced NotI and XhoI restriction sites flanking the $G_{11}\alpha$ coding sequence respectively. In the second step, the amplified receptor fragment was digested with HindIII/NotI and the $G_{11}\alpha$ fragment digested with NotI/XhoI. These fragments were purified and ligated into pcDNA 3 vector (Invitrogen) previously digested with HindIII/XhoI. The choice of intracellular loop 2 Leu to Asp mutants was based on the studies of Greasley et al., 2001. In the vast majority of class A GPCRs the equivalent position is also a hydrophobic amino acid (see FIG. 2). Such mutations were introduced into the fusion protein constructs using PCR mutagenesis by standard methods of site directed mutagenesis (Sambrook et al. and Carrillo et al., Manufacturers Kit etc.).

For co-immunoprecipitation and trFRET studies, c-myc (EQKLISEEDL; SEQ ID NO:44) or FLAG (DYKDDDDK; SEQ ID NO:45) epitopes were introduced immediately after the $NH_2$-terminal methionine. Each construct was fully sequenced before its expression and analysis (Mitchell et al., 1991; Mitchell et al., 1993).

Transient Transfection of HEK293 Cells

HEK293 cells were maintained in DMEM supplemented with 0.292 g/liter L-glutamine and 10% (v/v) newborn calf serum at 37° C. in a 5% $CO_2$ humidified atmosphere. Cells were grown to 60-80% confluency before transient transfection in 60 mm dishes. Transfection was performed using LipofectAMINE reagent (Life Technologies, Inc.) according to the manufacturer's instructions.

[$^{35}$S]GTPγS Binding

[$^{35}$S]GTPγS binding experiments were initiated by the addition of membranes containing defined amounts of the fusion constructs (see Results for details) to an assay buffer (20 mM HEPES (pH 7.4), 3 mM $MgCl_2$, 100 mM NaCl, 1 μM guanosine 5'-diphosphate, 0.2 mM ascorbic acid, 50 nCi [$^{35}$S]GTPγS) containing the indicated concentrations of receptor ligands. Non-specific binding was determined in the same conditions but in the presence of 100 μM GTPγS. Reactions were incubated for 15 min at 30° C. and were terminated by the addition of 0.5 ml of ice cold buffer, containing 20 mM HEPES (pH 7.4), 3 mM $MgCl_2$ and 100 mM NaCl. The samples were centrifuged at 16,000 g for 15 min at 4° C., and the resulting pellets were resuspended in solubilization buffer (100 mM Tris, 200 mM NaCl, 1 mM EDTA, 1.25% Nonidet P-40) plus 0.2% sodium dodecylsulfate. Samples were pre-cleared with Pansorbin (Calbiochem), followed by immuno-precipitation with CQ antiserum (Mitchell et al., 1993). Finally, the immunocomplexes were washed twice with solubilization buffer, and bound [$^{35}$S]GTPγS measured by liquid-scintillation spectrometry.

[$^3$H]Ligand Binding Studies

[$^3$H]prazosin binding studies, to monitor expression of the $\alpha_{1b}$-adrenoceptor containing constructs, were performed as in (Carillo, et al., 2002). [$^3$H]mepyramine binding assays, to monitor expression of the histamine H1 receptor containing constructs were initiated by the addition of 3 μg of cell membranes to an assay buffer (50 mM Tris-HCl, 100 mM NaCl, 3 mM $MgCl_2$, pH 7.4) containing [$^3$H]mepyramine (0.1-10 nM). Non-specific binding was determined in the presence of 100 μM mepyramine. Reactions were incubated for 30 min at 25° C., and bound ligand separated from free by vacuum filtration through GF/B filters. The filters were washed twice with assay buffer, and bound ligand estimated by liquid scintillation spectrometry.

[$Ca^{2+}$]$_i$ Imaging

EF88 cells were grown in DMEM supplemented with 10% (v/v) heat inactivated foetal bovine serum and L-glutamine (1 mM) in a 95% air and 5% $CO_2$ atmosphere at 37° C. A portion of the cells harvested during trypsinization were plated on to glass coverslips and after a 24 h growth period they were transfected using LipofectAMINE (Life Technologies Inc.) according to the manufacturers' instructions. After 3 h cells were washed twice with OPTIMEM 1 and then cultured in DMEM growth medium for a further 24 h. A total of 3 µg of pCDNA3 containing the relevant cDNA species were used to transfect each coverslip. Transfected EF88 cells were loaded with the $Ca^{2+}$-sensitive dye Fura-2 by incubation (15-20 min, 37° C.) under reduced light in DMEM growth medium containing the dye's membrane-permanent acetoxymethylester form (1.5 µM). Details of imaging studies and their analysis is described in Liu et al., 2002.

GPCR Co-Immunoprecipitation Studies

Co-immunoprecipitation studies using FLAG and c-myc tagged forms of the $\alpha_{1b}$-adrenoceptor and histamine H1 receptor constructs were performed as in (McVey et al., 2001). In the studies with the histamine H1 receptor 30 U/ml of endoglycosidase F were added.

Time Resolved Fluorescence Resonance Energy Transfer

Was performed on intact HEK293 cells using $Eu^{3+}$-labelled anti-c-myc antibodies and allophycocyanin-labelled anti-FLAG antibodies as described in (McVey et al., 2001).

Results

The present inventor has previously generated a fusion protein between the $\alpha_{1b}$-adrenoceptor and the $\alpha$ subunit of $G_{11}$ that binds both agonists and antagonists ligands including [$^3$H]prazosin (Carillo, et al., 2002). Addition of the agonist phenylephrine to membranes of HEK293 cells transfected to express this construct resulted in a large stimulation of the binding of [$^{35}$S]GTP$\gamma$S monitored following end of assay immunoprecipitation using an antiserum against the C-terminal decapeptide of $G_{11}\alpha$ (FIG. 4A).

Introduction of a Gly$^{208}$AlaG$_{11}\alpha$ mutant into the fusion protein essentially eliminated phenylephrine stimulation of [$^{35}$S]GTP$\gamma$S binding when membranes expressing equal amounts of this construct were used (FIG. 4A(2)) because this form of the G protein is unable to release bound GDP. However, this mutation did not alter the binding properties of either [$^3$H]prazosin or phenylephrine).

Previous studies have shown that mutation of hydrophobic amino acids in intracellular loop 2 of the $\alpha_{1b}$-adrenoceptor can eliminate agonist-mediated signal transduction (Greasley et al., 2001). The present inventor thus generated a fusion protein between Leu$^{151}$Asp $\alpha_{1b}$-adrenoceptor and $G_{11}\alpha$. (This bound both [$^3$H]prazosin and phenylephrine as the wild type fusion protein (not shown) but phenylephrine was again unable to stimulate binding of [$^{35}$S]GTP$\gamma$S (FIG. 4A(3)). However, co-expression of the two non-functional mutants reconstituted phenylephrine-mediated binding of [$^{35}$S]GTP$\gamma$S (FIG. 4A(4)) and when the membrane amounts employed contained twice as many [$^3$H]prazosin binding sites as used for each individual construct the level of agonist-mediated [$^{35}$S]GTP$\gamma$S was almost as high as when employing the wild type fusion construct (FIG. 4A(5)).

Reconstitution of function required co-expression of the two mutant fusions. If the two constructs were expressed in separate cell populations and either the cells mixed prior to membrane preparation or membranes prepared individually and then combined prior to assay, no agonist-stimulated binding of [$^{35}$S]GTP$\gamma$S was observed (FIG. 4B). Such results are consistent with the hypothesis that GPCR dimerization is required for agonist function. Furthermore, within the dimer, one GPCR element activates the G protein physically linked to the partner GPCR.

To extend this basic concept an equivalent set of experiments was performed using fusions between the histamine H1 receptor and $G_{11}\alpha$. The basic results were the same. The fusion containing wild type forms of both the GPCR and G protein produced a large stimulation of [$^{35}$S]GTP$\gamma$S binding in the presence of histamine (FIG. 5(1)). This was absent upon separate expression of either a histamine H1 receptor-Gly$^{208}$Ala $G_{11}\alpha$ fusion protein (FIG. 5(2)) or a fusion between Leu$^{133}$Asp histamine H1 receptor and wild type $G_{11}\alpha$ (FIG. 5 (3)). Co-expression of these two mutants again reconstituted agonist activation of the G protein (FIG. 5(4)). Again, following co-expression of the two mutants, membranes expressing a 2 fold higher number of [$^3$H]antagonist binding sites produced as high a level of [$^{35}$S]GTP$\gamma$S binding upon addition of the agonist histamine as the wild type histamine H1 receptor-$G_{11}\alpha$ fusion protein expressed in isolation (FIG. 5(5)).

As an extension to these studies the present inventors attempted to monitor functional reconstitution and dimerization in a single cell. To do so they employed $Ca^{2+}$ imaging using EF88 cells. EF88 cells are a line of mouse embryo fibroblasts that are derived from a $G_q\alpha/G_{11}\alpha$ double knock-out mouse (Mao et al., 1998; Yu and Hinkle, (1999). They thus require expression of both a functional GPCR and functional $Ca^{2+}$-mobilizing G protein to produce elevation of intracellular $[Ca^{2+}]$ (Liu et al., (2002; Stevens et al., 2001). Upon introduction of fusions between wild type forms of either the histamine H1 receptor or the $\alpha_{1b}$-adrenoceptor and $G_{11}\alpha$ agonists produced elevation of intracellular $[Ca^{2+}]$ (FIG. 6).

This occurred only in positively transfected cells. As EF88 cells are recalcitrant to transfection the present inventors co-transfected with enhanced green fluorescent protein (GFP) to allow visualization of the positively transfected cells. Only those cells that were positive for GFP responded to agonist ligands (FIG. 6b). For both the histamine H1 receptor and the $\alpha_{1b}$-adrenoceptor the fusions containing either the non agonist-responsive GPCR or the G protein mutant failed to elevate intracellular $[Ca^{2+}]$. However, co-expression of the pairs of non-functional fusions again resulted in effective signal generation (FIGS. 6a, 6b, 7a and 7b).

The present inventor has also demonstrated directly the ability of both the isolated GPCRs and the GPCR/G protein fusions to form dimers/oligomers. Constructs were N-terminally epitope tagged with either the c-myc or FLAG tags. Following co-expression in HEK293 cells of both tagged forms of the $\alpha_{1b}$-adrenoceptor, but not their separate expression followed by cell mixing, immunoprecipitation with anti-FLAG antibodies resulted in the presence of anti-c-myc immunoreactivity in the precipitate (FIG. 8a). SDS-PAGE demonstrated the presence of bands identified by the c-myc antibody of apparent size 53 kDa and 110 kDa that would be consistent with monomeric and dimeric forms of the $\alpha_{1b}$-adrenoceptor. Anti c-myc immunoreactivity was also observed near the top of the gel and this may represent either a higher-order oligomer or aggregated protein (FIG. 8a). When equivalent experiments were performed with the $\alpha_{1b}$-adrenoceptor-$G_{11}\alpha$ fusion protein similar results were obtained except that the anti-c-myc reactive bands were now of apparent mass 90 kDa and 200 kDa, consistent with the anticipated size of monomeric and dimeric forms of this fusion protein (FIG. 8A). Similar results were obtained for FLAG and c-myc tagged forms of the histamine H1 receptor (FIG. 8B). The monomeric form of the isolated receptor migrated as an approximately 50 kDa polypeptide with the dimeric form migrating as anticipated for a polypeptide of some 100 kDa (FIG. 8B). Again, as with the $\alpha_{1b}$-adrenoceptor, a series of higher molecular mass species were also detected. When using the histamine H1 receptor-$G_{11}\alpha$ fusion protein both the monomeric and dimeric species were also easily detected (FIG. 8b).

A series of issues have been raised about the meaning and validity of GPCR dimerization data that rely exclusively on co-immunoprecipitation (Milligan G, 2001; Salim et al., 2002). The present inventors thus monitored dimerization/oligomerization of both the isolated $\alpha_{1b}$-adrenoceptor and the $\alpha_{1b}$-adrenoceptor-$G_{11}\alpha$ fusion protein in intact HEK293 cells using time-resolved fluorescence resonance energy transfer (tr-FRET). When co-expressing c-myc and FLAG-tagged forms of either the isolated GPCR or the fusion protein a clear energy transfer signal was obtained upon addition of a combination of $Eu^{3+}$-labelled anti-c-myc antibodies, as energy donor and allophycocyanin (APC)-labelled anti-FLAG antibodies as energy acceptor (FIG. 9A). An energy transfer signal was not obtained when the tagged forms of the GPCR constructs were expressed in separate population of cells that were mixed prior to the addition of the antibodies. Equivalent results were obtained in HEK293 cells expressing N-terminally c-myc and FLAG-tagged forms of both the histamine H1 receptor and the histamine H1 receptor-$G_{11}$ fusion protein (FIG. 9B).

To examine the possibility of hetero-dimerisation between the histamine H1 receptor and the $\alpha_{1b}$-adrenoceptor and the mechanism of G protein activation by GPCR dimers the inventor co-expressed a FLAG-tagged form of the histamine H1 receptor and the c-myc-tagged form of the $\alpha_{1b}$-adrenoceptor. Following immunoprecipitation with anti-FLAG antibodies and SDS-PAGE, c-myc immunoreactivity was detected in polypeptides of apparent molecular mass 50 and 100 kDa consistent with the immunoprecipitation of histamine H1 receptor-$\alpha_{1b}$-adrenoceptor hetero-dimers that are only partially separated by the electrophoresis conditions employed (FIG. 11A). tr-FRET studies following co-expression of the FLAG-tagged form of the histamine H1 receptor and the c-myc-tagged form of the $\alpha_{1b}$-adrenoceptor confirmed the presence of histamine H1 receptor/$\alpha_{1b}$-adrenoceptor hetero-dimers at the cell surface (FIG. 11B) although the absolute level of the signal indicated that these hetero-dimers formed less efficiently than the corresponding homo-dimer pairs (see y-axis of FIGS. 9A and 9B compared to FIG. 11B). As in the homo-dimer studies no tr-FRET signal was observed when separate cell populations expressing each of these receptors were mixed prior to analysis (FIG. 11B).

Figure 7B:
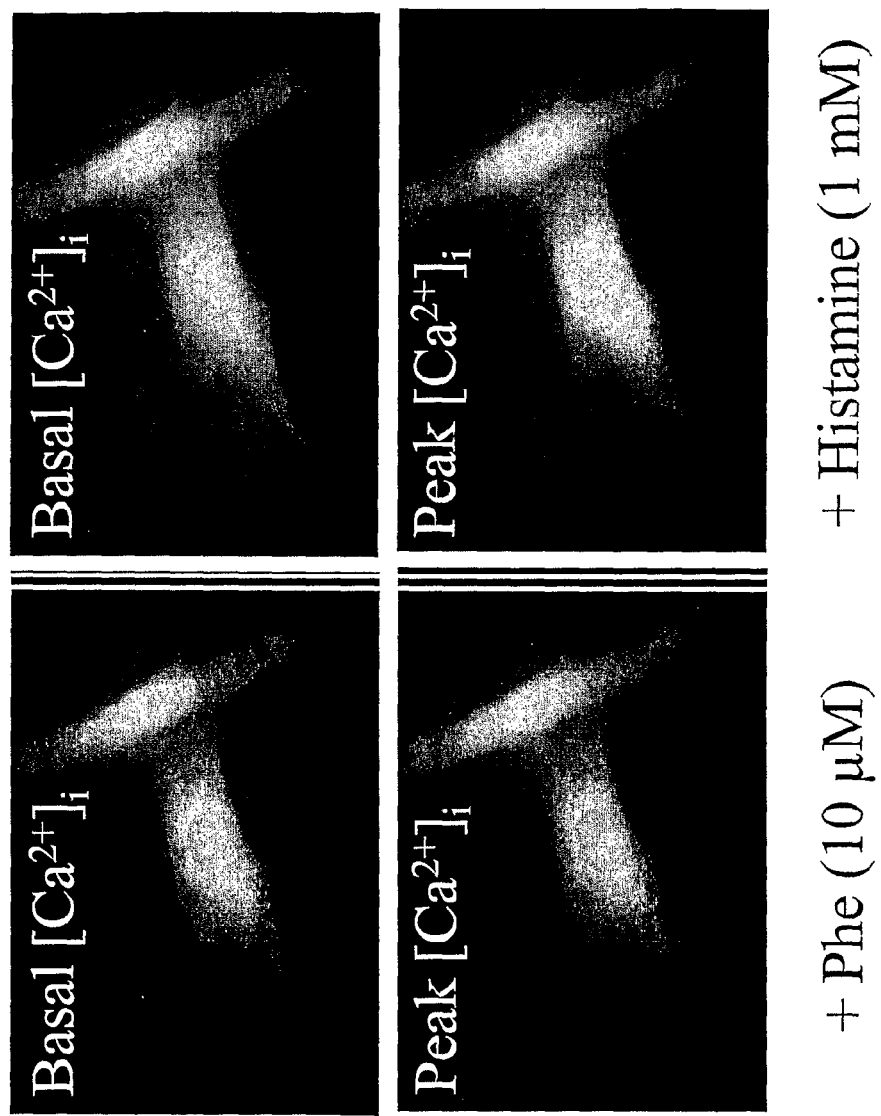

When $Leu^{133}Asp$ histamine H1 receptor-$G_{11}\alpha$ was co-expressed in EF88 cells with $\alpha_{1b}$-adrenoceptor-$Gly^{208}Ala$ $G_{11}\alpha$, phenylephrine was able to elevate intracellular $[Ca^{2+}]$ but histamine was not (FIG. 12A). This can only occur if the $\alpha_{1b}$-adrenoceptor activates the G protein physically linked to the $Leu^{133}Asp$ histamine H1 receptor. When the protocol was reversed by co-expression of $Leu^{151}Asp\alpha_{1b}$-adrenoceptor-$G_{11}\alpha$ and histamine H1 receptor-$Gly^{208}Ala$ $G_{11}\alpha$ histamine now caused elevation of intracellular $[Ca^{2+}]$ but phenylephrine did not (FIG. 7B). To extend this type of analysis the histamine H1 receptor-$G_{11}\alpha$ fusion was co-expressed with the isolated $Leu^{151}Asp$ $\alpha_{1b}$-adrenoceptor that is unable to activate G protein and thus stimulate binding of $[^{35}S]GTP\gamma S$. Histamine stimulation of $[^{35}S]GTP\gamma S$ binding was significantly reduced in comparison to membranes expressing the same level of only the histamine H1 receptor-$G_{11}\alpha$ fusion (FIG. 12A). Such data are consistent with the $Leu^{151}Asp$ $\alpha_{1b}$-adrenoceptor generating inactive hetero-dimers with histamine H1 receptor-$G_{11}\alpha$ and indicate that the histamine H1 receptor in the hetero-dimer does not activate the G protein physically associated with it. The remaining signal produced by histamine in the co-transfection reflects that some functional histamine H1 receptor-$G_{11}\alpha$ homo-dimer is still formed in the presence of $Leu^{151}Asp$ $\alpha_{1b}$-adrenoceptor. Indeed, when the inventor co-expressed histamine H1 receptor-$G_{11}\alpha$ with increasing amounts of $Leu^{151}Asp$ $\alpha_{1b}$-adrenoceptor cDNA, the ability of histamine to cause $[^{35}S]GTP\gamma S$ binding in membranes expressing the same number of histamine H1 receptor binding sites decreased as levels of $Leu^{151}Asp$ $\alpha_{1b}$-adrenoceptor cDNA were increased (FIG. 12A). Similar results were obtained following co-transfection of $Leu^{151}Asp$ $\alpha_{1b}$-adrenoceptor with the histamine H1 receptor-$G_{11}\alpha$ in EF88 cells. Histamine stimulation of intracellular $[Ca^{2+}]$ was reduced markedly (FIG. 12B).

Co-expression of two distinct GPCRs must result in the presence of the respective homo-dimers as well as providing the potential for hetero-dimer formation. The inventor wished to ensure that the reconstitution of $Ca^{2+}$ signalling observed upon co-expression of $Leu^{133}Asp$ histamine H1 receptor-$G_{11}\alpha$ with $\alpha_{1b}$-adrenoceptor-$Gly^{208}Ala$ $G_{11}\alpha$ did not reflect that only $\alpha_{1b}$-adrenoceptor and histamine H1 receptor homo-dimers were present and that the $\alpha_{1b}$-adrenoceptor-$Gly^{208}Ala$ $G_{11}\alpha$ homo-dimers were simply able to contact and activate $G_{11}$ linked to $Leu^{133}Asp$ histamine H1 receptor-$G_{11}\alpha$ homo-dimers. To enhance the levels of appropriately membrane targeted G protein he generated a construct in which $G_{11}\alpha$ was linked to the C-terminus of a c-myc-tagged form of the N-terminal and first transmembrane region of the $\alpha_{1b}$-adrenoceptor (c-myc-Nt-TM1$\alpha_{1b}$-$G_{11}\alpha$). When this was transfected into HEK293 cells, immunoblots of membrane fractions clearly demonstrated its expression as a doublet of 53 and 47 kDa whether detection was via anti-c-myc (FIG. 13A) or anti-G protein antisera (data not shown). Based on immunodetection by the anti-c-myc antibody levels of c-myc-Nt-TM1$\alpha_{1b}$-$G_{11}\alpha$ were significantly greater than of the c-myc-$\alpha_{1b}$-adrenoceptor-$G_{11}\alpha$ fusion protein (FIG. 13A). $[^{35}S]GTP\gamma S$ binding assays, at the end of which the c-myc-Nt-TM1$\alpha_{1b}$-$G_{11}\alpha$ construct was immunoprecipitated with anti-c-myc antibodies, confirmed this construct did not bind $[^{35}S]GTP\gamma S$ in response to phenylephrine (FIG. 13B). Parallel experiments showed that the anti-c-myc antibodies did capture phenylephrine stimulated binding of $[^{35}S]GTP\gamma S$ to the full length c-myc-tagged $\alpha_{1b}$-adrenoceptor-$G_{11}\alpha$ fusion protein (FIG. 13B). However, co-expression of c-myc-Nt-TM1$\alpha_{1b}$-$G_{11}\alpha$ with the isolated $\alpha_{1b}$-adrenoceptor equally did not result in significant stimulation of $[^{35}S]GTP\gamma S$ binding in anti-c-myc immunoprecipitates (FIG. 13B) and this was also true when c-myc-Nt-TM1$\alpha_{1b}$-$G_{11}\alpha$ was co-expressed with the $\alpha_{1b}$-adrenoceptor-$Gly^{208}Ala G_{11}\alpha$ fusion protein (FIG. 13B). Thus, simply increasing the concentration of membrane-associated G protein did not allow $\alpha_{1b}$-adrenoceptor or $\alpha_{1b}$-adrenoceptor-fusion protein homo-dimers to activate this G protein. This argues strongly that the data from the co-expression of the pairs of inactive histamine H1 receptor and $\alpha_{1b}$-adrenoceptor receptor G protein fusions must results from trans-activation within the hetero-dimer.

Example of a Fluorometric Imaging Plate Reader (FLIPR) Assay for the Measurement of Intracellular Calcium Concentration Target Receptor (experimental) and pCMV (negative control) stably transfected cells from respective clonal lines are seeded into poly-D-lysine pretreated 96-well plates (Becton-Dickinson, #356640) at $5.5\times10^4$ cells/well with complete culture medium (DMEM with 10% FBS, 2 mM L-glutamine, 1 mM sodium pyruvate) for assay the next day. To prepare Fluo4-AM (Molecular Probe, #F14202) incubation buffer stock, 1 mg Fluo4-AM is dissolved in 467 μl DMSO and 467 μl Pluronic acid (Molecular Probe, #P3000) to give a 1 mM stock solution that can be stored at −20° C. for a month. Fluo4-AM is a fluorescent calcium indicator dye.

Candidate compounds are prepared in wash buffer (1×HBSS/2.5 mM Probenicid/20 mM HEPES at pH 7.4).

At the time of assay, culture medium is removed from the wells and the cells are loaded with 100 μl of 4 μM Fluo4-AM/2.5 mM Probenicid (Sigma, #P8761)/20 mM HEPES/complete medium at pH 7.4. Incubation at 37° C./5% $CO_2$ is allowed to proceed for 60 min.

After the 1 hr incubation, the Fluo4-AM incubation buffer is removed and the cells are washed 2× with 100 μl wash buffer. In each well is left 100 μl wash buffer. The plate is returned to the incubator at 37° C./5% $CO_2$ for 60 min.

FLIPR (Fluorometric Imaging Plate Reader; Molecular Device) is programmed to add 50 μl candidate compound on the $30^{th}$ second and to record transient changes in intracellular calcium concentration ($[Ca^{2+}]$) evoked by the candidate compound for another 150 seconds. Total fluorescence change counts are used to determine agonist activity using the FLIPR software. The instrument software normalizes the fluorescent reading to give equivalent initial readings at zero.

In some embodiments, the cells comprising Target Receptor further comprise promiscuous G alpha 15/16 or the chimeric Gq/Gi alpha unit.

Although the foregoing provides a FLIPR assay for agonist activity using stably transfected cells, a person of ordinary skill in the art would readily be able to modify the assay in order to characterize antagonist activity. Said person of ordinary skill in the art would also readily appreciate that, alternatively, transiently transfected cells could be used.

Example of a Melanophore Assay to Detect Ligand Binding

Melanophores are skin cells found in lower vertebrates. They contain pigmented organelles termed melanosomes. Melanophores are able to redistribute these melanosomes along a microtubule network upon G-protein coupled receptor (GPCR) activation. The result of this pigment movement is an apparent lightening or darkening of the cells. In melanophores, the decreased levels of intracellular cAMP that result from activation of a Gi-coupled receptor cause melanosomes to migrate to the center of the cell, resulting in a dramatic lightening in color. If cAMP levels are then raised, following activation of a Gs-coupled receptor, the melanosomes are re-dispersed and the cells appear dark again. The increased levels of diacylglycerol that result from activation of Gq-coupled receptors can also induce this re-dispersion. In addition, the technology is also suited to the study of certain receptor tyrosine kinases. The response of the melanophores takes place within minutes of receptor activation and results in a simple, robust color change. The response can be easily detected using a conventional absorbance microplate reader or a modest video imaging system. Unlike other skin cells, the melanophores derive from the neural crest and appear to express a full complement of signaling proteins. In particular, the cells express an extremely wide range of G-proteins and so are able to functionally express almost all GPCRs.

Melanophores can be utilized to identify compounds, including natural ligands, against GPCRS. This method can be conducted by introducing test cells of a pigment cell line capable of dispersing or aggregating their pigment in response to a specific stimulus and expressing an exogenous clone coding for the GCPR. A stimulant, e.g., melatonin, sets an initial state of pigment disposition wherein the pigment is aggregated within the test cells if activation of the GPCR induces pigment dispersion. However, stimulating the cell with a stimulant to set an initial state of pigment disposition wherein the pigment is dispersed if activation of the GPCR induces pigment aggregation. The test cells are then contacted with chemical compounds, and it is determined whether the pigment disposition in the cells changed from the initial state of pigment disposition. Dispersion of pigments cells due to the candidate compound, including but not limited to a ligand, coupling to the GPCR will appear dark on a petri dish, while aggregation of pigments cells will appear light.

Materials and Methods will be followed according to the disclosure of U.S. Pat. No. 5,462,856 and U.S. Pat. No. 6,051, 386. These patent disclosures are hereby incorporated by reference in their entirety.

The cells are plated in 96-well plates (one receptor per plate). 48 hours post-transfection, half of the cells on each plate are treated with 10 nM melatonin. Melatonin activates an endogenous Gi-coupled receptor in the melanophores and causes them to aggregate their pigment. The remaining half of the cells are transferred to serum-free medium 0.7× L-15 (Gibco). After one hour, the cells in serum-free media remain in a pigment-dispersed state while the melatonin-treated cells are in a pigment-aggregated state. At this point, the cells are treated with a dose response of the selected test compound. If the plated GPCRs bound to the selected test compound, the melanophores would be expected to undergo a color change in response to the compound. If the receptor were either a Gs or Gq coupled receptor, then the melatonin-aggregated melanophores would undergo pigment dispersion. In contrast, if the receptor was a Gi-coupled receptor, then the pigment-dispersed cells would be expected to undergo a dose-dependent pigment aggregation.

Discussion

By employing fusion proteins between both the $\alpha_{1b}$-adrenoceptor and the histamine H1 receptor with the G protein $G_{11}\alpha$ the present inventors now show that these GPCRs dimerize and that this is not compromised by addition of the G protein to the C-terminal tail of the GPCR. Equally, by employing trFRET to detect GPCR dimers/oligomers in intact cells they were able to demonstrate the presence of these complexes at the cell surface. This also was not compromised by the addition of the G protein sequence to the GPCRs. Furthermore, by introducing mutations that prevent agonist activation of the G protein into either the GPCR or the G protein the inventors produced pairs of non-functional fusion proteins that were able to restore agonist-mediated function when co-expressed. Functional reconstitution was monitored in two ways. Firstly, agonists were able to produce elevation of intracellular $[Ca^{2+}]$ in EF88 cells only following co-expression of two mutants that were each non-functional in isolation. EF88 cells lack expression of phospholipase C-coupled G proteins and thus it is necessary to introduce both a suitable GPCR and G protein into these cells to generate a $Ca^{2+}$ signal. This assay had the obvious benefit that $Ca^{2+}$ imaging allowed the inventors to monitor functional dimerization in single cells. One of the earliest steps that can be measured in the signal transduction cascade is agonist-induced guanine nucleotide exchange on the G protein. This can be monitored conveniently by the binding of $[^{35}S]GTP\gamma S$. In all the $[^{35}S]GTP\gamma S$ binding assays the inventors initially measured the level of expression of each of the GPCR G protein fusions by using saturation $[^3H]$antagonist binding studies. This allowed them to add membrane amounts containing defined quantities of the constructs to the assays. The inventors have previously demonstrated that there is a linear increase in agonist-stimulated $[^{35}S]GTP\gamma S$ binding with addition of increasing amounts of a GPCR-$G_{11}\alpha$ fusion protein (Stevens et al., 2001). When co-expressing the histamine H1 receptor-Gly$^{208}$Ala G$_{11}\alpha$ and Leu$^{133}$Asp histamine H1 receptor-G$_{11}\alpha$ fusion proteins, it required the presence of twice the number of [$^3$H]antagonist binding sites to generate approximately the same amount of agonist-stimulated [$^{35}$S] GTPγS binding as when only the wild type histamine H1 receptor-G$_{11}\alpha$ fusion protein was expressed. This provides good evidence that the functional element is a dimer or a higher order oligomer. If the functional histamine H1 receptor is a dimer, then stochastically, when co-expressing the two non-functional mutant fusions, half of the dimers produced should be non-functional because they will be homodimers of either histamine H1 receptor-Gly$^{208}$Ala G$_{11}\alpha$ or Leu$^{133}$Asp histamine H1 receptor-G$_{11}\alpha$. Only 50% of the dimers would be expected to be functional heterodimers containing one copy of histamine H1 receptor-Gly$^{208}$Ala G$_{11}\alpha$ and one of Leu$^{133}$Asp histamine H1 receptor-G$_{11}\alpha$ (FIG. 10). These studies also support the idea that, as for the class C GPCRs, aminergic class A GPCRs function via a trans-activation mechanism. The copy of the G protein in the dimer that can be activated is linked to the non-functional form of the GPCR whereas the functional form of the GPCR is associated with non-functional G protein.

In order to further support this mechanism, the inventor took advantage of the known capacity of structural related GPCRs to form hetero-dimers. Initial studies demonstrated that when co-expressed the histamine H1 receptor and the $\alpha_{1b}$-adrenoceptor could be co-immunoprecipitated. Furthermore, co-expression in EF88 cells of Leu$^{133}$Asp histamine H1 receptor-G$_{11}\alpha$ and $\alpha_{1b}$-adrenoceptor-Gly$^{208}$AlaG$_{11}\alpha$ resulted in phenylephrine but not histamine-mediated elevation of [Ca$^{2+}$]i. This can only occur if the $\alpha_{1b}$-adrenoceptor activates the G protein physically linked to the inactive histamine H1 receptor (FIG. 2). When the experiment was reversed such that the inactive $\alpha_{1b}$-adrenoceptor was linked to the wild type G protein and the wild type histamine H1 receptor linked to the mutant G protein now histamine was functional but phenylephrine was not. The inventor extended this idea by examining the effectiveness of histamine to stimulate binding of [$^{35}$S]GTPγS when the histamine H1 receptor fusion protein was co-expressed with increasing amounts of the isolated but inactive Leu$^{151}$Asp $\alpha_{1b}$-adrenoceptor. The effect of histamine was reduced. Such information is consistent with the concept than increasing levels of a histamine H1 receptor-G$_{11}\alpha$-Leu$^{151}$Asp $\alpha_{1b}$-adrenoceptor hetero-dimer reduces amounts of the histamine H1 receptor-G$_{11}\alpha$ homo-dimer and that histamine binding to the hetero-dimer is unable to activate the G protein that is physically associated with the histamine H1 receptor. In this situation phenylephrine was inactive as Leu$^{151}$Asp $\alpha_{1b}$-adrenoceptor is unable to stimulate any G protein. A number of reports have indicated that GPCR-G protein fusions can interact with and activate endogenously expressed G proteins as well as the G protein element of the fusion (Burt et al., 1998, J. Biol. Chem. 273, 10367-10375; Molinari et al, 2003 J. Biol. Chem. 278, 15778-15788). However, in these studies the GPCR-G protein fusions have been expressed at very high levels that are within the range in which non-specific 'bystander' (Mercier et al., 2002 J. Biol. Chem. 277, 44925-44931) effects have been reported, due to physical proximity in the membrane. Use of EF88 cells eliminated the possibility of interaction with endogenous G proteins as they do not express G$_q\alpha$ or G$_{11}\alpha$ and thus effects have to reflect activation of the fused G proteins. Moreover, following introduction of the Gly$^{208}$Ala mutation into the G protein element of the fusions agonist stimulation of [$^{35}$S]GTPγS binding in membranes of transfected HEK293 cells was virtually abolished. This indicates that at the level of expression achieved, there was virtually no activation of endogenous G$_q\alpha$ or G$_{11}\alpha$ in HEK293 cells even though both are expressed. In the hetero-dimerisation experiments in HEK293 cells excess G protein is introduced in a 1:1 molar ratio with the second GPCR due to the 1:1 stoichiometry of GPCR and G protein defined by the fusion. To assess if the results could be ascribed simply to the presence of the extra G protein the inventor provided extra G protein via an alternate strategy. To do so he generated a form of G$_{11}\alpha$ linked to the N-terminal and first transmembrane region of the $\alpha_{1b}$-adrenoceptor. Equivalent constructs for other G proteins have been employed previously (Lee et al., 1999 Biochemistry 38, 13801-13809, Guzzi et al., 2001 Biochem J. 355, 323-331, Molinari et al., 2003 J. Biol. Chem. 278, 15778-15788) and it has been suggested that the link to a transmembrane α helix provides the G protein in a particularly effective orientation for activation (Molinari et al., 2003 as above). Although this construct could be expressed to markedly higher levels than the $\alpha_{1b}$-adrenoceptor-G$_{11}\alpha$ fusions, the G protein was not activated by phenylephrine, whether expressed alone or in combination with either the isolated $\alpha_{1b}$-adrenoceptor or an $\alpha_{1b}$-adrenoceptor-G$_{11}\alpha$ fusion. These studies confirmed that the reconstitution of signal with co-expression of non-functional pairs of GPCR-G protein fusions must reflect an internal transactivation within the reconstituted dimer.

TABLE 1

| | |
|---|---|
| gastrointestinal tract smooth muscle | motility of stomach and intestines |
| gastrointestinal tract ganglionic nerve fibers | motility of stomach and intestines |
| urinary tract smooth muscle | ureter function and urinary bladder function |
| salivary gland | salivary secretion |
| alpha cells of the pancreas | secretion of glucagons |
| beta cells of the pancreas | secretion of insulin |
| uterine smooth muscle | uterine contraction |
| heart muscle | contractility of heart muscle |
| vascular smooth muscle | contractility of smooth muscle |
| adipocytes | lipolysis |
| platelets | platelet aggregation in response to blood vessel injury |
| skeletal neuromuscular junction | skeletal muscle contractility |
| bronchial smooth muscle | respiration |
| nasal mucosal blood vessels | mucosa volume |
| trigone muscle of bladder and urethra | urinary outflow |
| chondrocytes | cartilage formation |
| ciliary body of the eye | aqueous humor production |
| thyroid | thyroid hormone secretion |
| mast cells | immediate hypersensitivity reactions |

TABLE 1-continued

| | |
|---|---|
| basophils | immediate hypersensitivity reactions |
| osteoblasts | bone remodeling |
| osteoclasts | bone remodeling |
| brain capillary endothelial cells | permeability of blood-brain barrier |
| T cells | immune response |
| B cells | immune response |
| kidney proximal tubular epithelial cells | organic acids exchange |
| neutrophils | immune response |
| eosinophils | immune response |
| monocytes | immune response |
| kidney late distal tubule | organic bases exchange |
| collecting duct principal cells | organic bases exchange |
| kidney granular juxtaglomerular cells | secretion of rennin |
| peripheral postganglionic adrenergic neurons | sympathetic function |
| hepatocytes | synthesis of cholesterol and lipoprotein |
| gastrointestinal parietal cells | secretion of stomach acid |
| gastrointestinal superficial epithelial cells | secretion of cytoprotective factors, mucus and bicarbonate |
| epidermal cells | skin maintenance |
| bone marrow stem cells | erythropoesis production |
| angle structures of the eye | aqueous humor outflow |
| uveoscleral structures of eye | aqueous humor outflow |
| suprachiasmatic nucleus | circadian rhythm |
| baroreceptors | blood pressure |
| basal ganglia | movement control |
| periaqueductal grey and dorsal horn of spinal cord | nociception |
| area postrema | vomiting |
| thalamus | sensorimotor processing and arousal |
| sensorimotor cerebral cortex | sensorimotor processing |
| spinal cord motor neurons | motor function control |
| dorsal root ganglion neurons | sensory information transmission |
| oligodendrocytes | neuron myelin sheath production |
| nucleus basalis | cognition and memory |
| nucleus accumbens | addictive cravings |
| lateral reticular formation of medulla | vomiting |
| hypothalamic neurons containing growth hormone releasing factor (GHRH) | secretion of GHRH |
| hypothalamic neurons containing somatostatin | secretion of somatostatin |
| hypothalamic neurons containing thyrotropin-releasing hormone (TRH) | secretion of TRH |
| hypothalamic neurons containing gonadotropin releasing hormone (GnRH) | secretion of GnRH |
| hypothalamic neurons containing corticotropin releasing factor (CRF) | secretion of CRF |
| anterior pituitary somatotropes | secretion of growth hormone |
| anterior pituitary lactotropes | secretion of prolactin |
| anterior pituitary gonadotropes | secretion of luteinizing hormone |
| anterior pituitary gonadotropes | secretion of follicle stimulating hormone |
| anterior pituitary corticotropes | secretion of adrenocorticotropic hormone |
| leydig cells of the testes | secretion of testosterone |
| sertoli cells of the testes | spermatogenesis |
| granulosa cells of the ovary | synthesis of estrogen |
| theca cells of the ovary | synthesis of estrogen |
| synovium | joint function |
| amygdala | modulation of emotion |
| pineal gland | regulation of circadian rhythm |
| nucleus of the solitary tract | cardiovascular regulation |
| caudal ventrolateral medulla | cardiovascular regulation |
| rostral ventrolateral medulla | vasopressor activity |
| parabrachial nucleus | taste aversion response and nociceptive response |
| entorhinal cortex | cognition |
| pyriform cortex | cognition |
| temporal cortex | memory acquisition |
| frontal cortex | regulation of emotional response and memory acquisition |
| parietal cortex | visual acuity, touch perception, and voluntary movement |
| occipital cortex | visual acuity |
| hippocampus | learning and memory |
| dentate gyrus | learning and memory |
| midbrain reticular formation | arousal |
| supraoptic nucleus of the hypothalamus | reproductive functions |
| magnocellular of the hypothalamus | modulation of stress, blood pressure and lactation |
| parvocellular neurons of the hypothalamus | metabolism |

TABLE 1-continued

| | |
|---|---|
| arcuate nucleus of the hypothalamus | release of pituitary hormones |
| trigeminal area | cerebral vessel dilation and blood pressure |
| cerebral blood vessels | cerebral vessel dilation |
| brain stem | breathing, heart rate, startle responses, sweating, blood pressure, digestion and body temperature |
| ventral lamina terminalis | blood pressure |
| vagus nerve | blood pressure and heart rate |
| nucleus of the solitary tract | blood pressure |
| adrenal medulla | catecholamine response to stress |
| adrenal cortex | stress-induced corticosterone release |
| locus coeruleus | arousal and response to stress |
| substantia nigra | control of body movement |
| ventral tegmental area | control of body movement |
| olfactory bulb | odor perception |
| median eminence of hypothalamus | pituitary function |
| raphe nuclei | sleep and arousal |
| habenula | sexual activity |
| cerebellum | control of body movement |
| posterior hypothalamus | intestinal motility and blood pressure |
| dorsal medulla | blood pressure |
| lateral hypothalamus | food intake and stomach acid secretion |
| rostral hypothalamus | heart rate |
| pontine-medullary reticular formation | respiration and heart rate |
| medulla | respiration and heart rate |
| mesencephalon | heart rate |
| ventral hypothalamus | response to stress |
| paraventricular nucleus of hypothalamus | response to stress |
| preoptic area of hypothalamus | sexual activity |
| mammillary region | food intake |
| perifornical area of hypothalamus | food intake |
| ventromedial hypothalamus | food intake |
| pons | reticular formation |
| septum | emotional control |
| pedunculopontine tegmental nucleus | arousal |
| astrocytes | neuronal metabolism |
| microglia | response to neuronal injury |
| choroid plexus | production of cerebrospinal fluid |
| Schwann cells | myelination of peripheral nerves |
| endoneurium | production of connective tissue nerve sheath |
| lateral spinothalamic pathway | response to pain and temperature stimuli |
| ventral spinothalamic pathway | touch sensation |
| dorsal column-medial lemniscal pathway | touch sensation |
| free nerve endings | response to pain and temperature |
| hair follicle endings | touch sensation |
| Krause's end-bulb | temperature sensation |
| Meissner's corpuscles | touch-pressure sensation |
| Merkel's disk | touch-pressure sensation |
| Pacinian corpuscle | touch-pressure sensation |
| Ruffini's corpuscle | temperature sensation |
| retina | visual acuity |
| parathyroid gland | calcium balance |
| placenta | placental activity |
| skeletal muscle fibers | muscle contraction |
| copora cavernosum | genital vasodilation |
| corticospinal tract | movement control |
| motor cerebral cortex | movement control |
| postganglionic neurons | control of blood pressure and adrenal activity |
| intramural ganglion | distal colon peristalsis |
| hypogastric plexus | control of urethral and anal sphincters |
| pelvic plexus | genital vasodilatation and penile erection |
| vesical plexus | urinary bladder control |
| celiac plexus | intestinal peristolisis. |

REFERENCES

1. Bouvier, M. (2001) Nat. Rev. Neurosci. 2, 274-286.
2. Carrillo J. J., Stevens P. A. and Milligan G. (2002) J. Pharmacol. Exp. Ther. 302, 1080-1088.
3. Devi, L. A. (2001) Trends Pharmacol. Sci. 22, 532-537.
4. Duthey B., Caudron S., Perroy J., Bettler B., Fagni L., Pin J. P., Prezeau L. (2002) J Biol. Chem. 277, 3236-3241.
5. George S. R., O'Dowd B. F., Lee S. P., (2002) Nat Rev Drug Discov. 1, 808-820.
6. Gohla A., Offermanns S., Wilkie T. M. and Schultz G. (1999) *J. Biol. Chem.* 274, 17901-17907.
7. Greasley P. J., Fanelli F., Scheer A., Abuin L., Nenniger-Tosato M., DeBenedetti P. G., Cotecchia S. (2001)
8. Lee D K, et al., Orphan-G-protein coupled receptors in CND, Curr Opin, Pharmacol. (2001) 1, 31-39.
9. Lee C., Ji I., Ryu K., Song Y., Conn P. M., Ji T H. (2002) J Biol Chem 277, 15795-15800.
10. Liu S., Carrillo J. J., Pediani J. and Milligan G. (2002) J. Biol. Chem. 277, 25707-25714.
11. Mao J., Yuan H., Xie W., Simon M. I. and Wu D. (1998) *J. Biol. Chem.* 273, 27118-27123.
12. McVey M., Ramsay D., Kellett E., Rees S., Wilson S., Pope A. J. and Milligan G. (2001) J. Biol. Chem. 276, 14092-14099.
13. Milligan G. (2000) Trends Pharmacol. Sci. 21: 24-28.
14. Milligan G (2001) J. Cell Sci. 114, 1265-1271.
15. Milligan G. (2002) Methods Enzymol. 343: 260-273.
16. Mitchell F. M., Buckley N. J. and Milligan G. (1993) Biochem. J. 293, 495-499.
17. Mitchell, F. M., Mullaney, I., Godfrey, P. P., Arkinstall, S. J., Wakelam, M. J. O. and Milligan, G. (1991) FEBS Lett. 287, 171-174.
18. Offermanns S., Zhao L. P., Gohla A., Sarosi I., Simon M. I. and Wilkie T. M. (1998) *EMBO J.* 17, 4304-4312
19. Salim K., Fenton T., Bacha J., Urien-Rodriguez H., Bonnert T., Skynner H. A., Watts E., Kerby J., Heald, A., Beer M., McAllister G. and Guest P. C. (2002) J Biol. Chem. 277, 15482-15485.
20. Stevens P. A., Pediani J., Carrillo J. J. and Milligan G. (2001) J. Biol. Chem. 276, 35883-35890.
21. Yu R. and Hinkle P. M. (1999) *J. Biol. Chem.* 274, 15745-15750.

---

The invention claimed is:

1. A GPCR oligomer comprising:
   (a) a first GPCR associated with a first G-protein wherein the first GPCR has a modified amino acid sequence compared to a wild-type GPCR sequence so as to render it non-functional with respect to the first G-protein; and;
   (b) a second GPCR associated with a second G-protein wherein the second G-protein is non-functional, wherein the wild-type form of the first GPCR is different to the second GPCR.

2. The GPCR oligomer of claim 1, wherein the first GPCR and first G-protein are associated as a fusion protein, and/or wherein the second GPCR and second G-protein are associated as a fusion protein.

3. The GPCR oligomer of claim 1, wherein the amino acid sequence of the first GPCR is modified within the $2^{nd}$ intracellular loop.

4. The GPCR oligomer of claim 1, wherein the amino acid sequence of the first GPCR is modified by amino acid residue substitution.

5. The GPCR oligomer of claim 1, wherein the second G-protein has a modified amino acid sequence compared to a wild-type G-protein so as to render it non-functional.

6. An isolated cell membrane comprising: (a) a first GPCR associated with a first G-protein wherein the first GPCR has a modified amino acid sequence compared to a wild-type GPCR sequence so as to render it non-functional with respect to the first G-protein; and,
   (b) a second GPCR associated with a second G-protein wherein the second G-protein is non-functional, wherein the wild-type form of the first GPCR is different to the second GPCR.

7. A eukaryotic cell comprising:
   a plasma membrane comprising: (a) a first GPCR associated with a first G-protein wherein the first GPCR has a modified amino acid sequence compared to a wild-type GPCR sequence so as to render it non-functional with respect to the first G-protein; and,
   (b) a second GPCR associated with a second G-protein wherein the second G-protein is non-functional, wherein the wild-type form of the first GPCR is different to the second GPCR.

8. The eukaryotic cell of claim 7, wherein said eukaryotic cell is a mammalian cell.

9. A method of making a cell comprising:
   (a) expressing a first nucleic acid construct in said cell, said nucleic acid construct encoding a first GPCR/G-protein fusion protein wherein the GPCR is mutated as compared to the wild-type GPCR thereby rendering it non-functional with respect to its G-protein;
   (b) expressing a second nucleic acid construct in said cell, said second nucleic acid construct encoding a second GPCR/G-protein fusion protein wherein the G-protein is mutated as compared to the wild-type G-protein thereby rendering it non-functional; and
   wherein the wild type form of the first GPCR is different to the second GPCR.

10. A method of screening comprising:
    a) contacting a compound with a cell expressing a GPCR oligomer comprising (i) a first GPCR associated with a G-protein wherein the first GPCR has a modified amino acid sequence compared to the wild-type GPCR sequence so as to render it non-functional with respect to the first G-protein; and (ii) a second GPCR associated with a G-protein wherein the G-protein is modified so that it is non-functional, wherein the wild-type form of the first GPCR is different to the second GPCR;
    b) detecting the presence of a cellular signal resulting from contact between said compound and said GPCR oligomer; and
    c) determining an effect said compound has on said cellular signal.

11. A method according to claim 10 wherein said cellular signal is determined using a reporter assay.

* * * * *

SEQUENCE LISTING

```
<160> NUMBER OF SEQ ID NOS: 45

<210> SEQ ID NO 1
<211> LENGTH: 11
<212> TYPE: PRT
<213> ORGANISM: Homo sapiens

<400> SEQUENCE: 1

Asp Arg Tyr Trp Ala Ile Thr Asp Pro Ile Asp
1               5                   10

<210> SEQ ID NO 2
<211> LENGTH: 11
<212> TYPE: PRT
<213> ORGANISM: Mus sp.

<400> SEQUENCE: 2

Asp Arg Tyr Trp Ala Ile Thr Asp Ala Val Glu
1               5                   10

<210> SEQ ID NO 3
<211> LENGTH: 11
<212> TYPE: PRT
<213> ORGANISM: Unknown
<220> FEATURE:
<223> OTHER INFORMATION: Rabbit 5HT1D receptor

<400> SEQUENCE: 3

Asp Arg Tyr Trp Ala Ile Thr Asp Ala Leu Glu
1               5                   10

<210> SEQ ID NO 4
<211> LENGTH: 11
<212> TYPE: PRT
<213> ORGANISM: Rattus sp.

<400> SEQUENCE: 4

Asp Arg Tyr Val Ala Ile Gln Asn Pro Ile His
1               5                   10
```

```
<210> SEQ ID NO 5
<211> LENGTH: 11
<212> TYPE: PRT
<213> ORGANISM: Rattus sp.

<400> SEQUENCE: 5

Asp Arg Tyr Val Ala Ile Arg Asn Pro Ile Glu
1               5                   10

<210> SEQ ID NO 6
<211> LENGTH: 11
<212> TYPE: PRT
<213> ORGANISM: Mus sp.

<400> SEQUENCE: 6

Asp Arg Tyr Tyr Ala Ile Cys Cys Gln Pro Leu
1               5                   10

<210> SEQ ID NO 7
<211> LENGTH: 11
<212> TYPE: PRT
<213> ORGANISM: Rattus sp.

<400> SEQUENCE: 7

Asp Arg Tyr Leu Leu Ile Leu Ser Pro Leu Arg
1               5                   10

<210> SEQ ID NO 8
<211> LENGTH: 11
<212> TYPE: PRT
<213> ORGANISM: Bos sp.

<400> SEQUENCE: 8

Asp Arg Tyr Ile Gly Val Ser Tyr Pro Leu Arg
1               5                   10

<210> SEQ ID NO 9
<211> LENGTH: 11
<212> TYPE: PRT
<213> ORGANISM: Unknown
<220> FEATURE:
<223> OTHER INFORMATION: Hamster alpha1b adrenergic receptor

<400> SEQUENCE: 9

Asp Arg Tyr Ile Gly Val Arg Tyr Ser Leu Gln
1               5                   10

<210> SEQ ID NO 10
<211> LENGTH: 11
<212> TYPE: PRT
<213> ORGANISM: Rattus sp.

<400> SEQUENCE: 10

Asp Arg Tyr Trp Ala Val Ser Arg Ala Leu Glu
1               5                   10

<210> SEQ ID NO 11
<211> LENGTH: 11
<212> TYPE: PRT
<213> ORGANISM: Homo sapiens

<400> SEQUENCE: 11

Asp Arg Tyr Leu Ala Ile Thr Ser Pro Phe Arg
1               5                   10
```

```
<210> SEQ ID NO 12
<211> LENGTH: 11
<212> TYPE: PRT
<213> ORGANISM: Bos sp.

<400> SEQUENCE: 12

Asp Arg Tyr Leu Ala Ile Thr Ser Pro Phe Lys
1               5                   10

<210> SEQ ID NO 13
<211> LENGTH: 11
<212> TYPE: PRT
<213> ORGANISM: Mus sp.

<400> SEQUENCE: 13

Asp Arg Tyr Leu Ala Val Thr Asn Pro Leu Arg
1               5                   10

<210> SEQ ID NO 14
<211> LENGTH: 11
<212> TYPE: PRT
<213> ORGANISM: Homo sapiens

<400> SEQUENCE: 14

Asp Arg Tyr Leu Arg Val Lys Ile Pro Leu Arg
1               5                   10

<210> SEQ ID NO 15
<211> LENGTH: 11
<212> TYPE: PRT
<213> ORGANISM: Homo sapiens

<400> SEQUENCE: 15

Asp Arg Tyr Leu Arg Val Lys Leu Thr Val Arg
1               5                   10

<210> SEQ ID NO 16
<211> LENGTH: 11
<212> TYPE: PRT
<213> ORGANISM: Mus sp.

<400> SEQUENCE: 16

Asp Arg Tyr Phe Ser Val Thr Arg Pro Leu Ser
1               5                   10

<210> SEQ ID NO 17
<211> LENGTH: 11
<212> TYPE: PRT
<213> ORGANISM: Homo sapiens

<400> SEQUENCE: 17

Asp Arg Tyr Phe Cys Val Thr Lys Pro Leu Thr
1               5                   10

<210> SEQ ID NO 18
<211> LENGTH: 11
<212> TYPE: PRT
<213> ORGANISM: Mus sp.

<400> SEQUENCE: 18

Asp Arg Tyr Phe Ser Ile Thr Arg Pro Leu Thr
1               5                   10

<210> SEQ ID NO 19
```

```
<211> LENGTH: 11
<212> TYPE: PRT
<213> ORGANISM: Homo sapiens

<400> SEQUENCE: 19

Asp Arg Tyr Ile Thr Ile Phe His Ala Leu Arg
1               5                   10

<210> SEQ ID NO 20
<211> LENGTH: 11
<212> TYPE: PRT
<213> ORGANISM: Homo sapiens

<400> SEQUENCE: 20

Asp Arg Tyr Leu Ala Ile Val His Pro Met Lys
1               5                   10

<210> SEQ ID NO 21
<211> LENGTH: 11
<212> TYPE: PRT
<213> ORGANISM: Homo sapiens

<400> SEQUENCE: 21

Asp Arg Tyr Leu Ala Leu Val Lys Thr Met Ser
1               5                   10

<210> SEQ ID NO 22
<211> LENGTH: 11
<212> TYPE: PRT
<213> ORGANISM: Mus sp.

<400> SEQUENCE: 22

Asp Arg Tyr Leu Ser Ile Val His Ala Thr Gln
1               5                   10

<210> SEQ ID NO 23
<211> LENGTH: 11
<212> TYPE: PRT
<213> ORGANISM: Homo sapiens

<400> SEQUENCE: 23

Asp Arg Tyr Leu Ala Ile Val His Ala Thr Asn
1               5                   10

<210> SEQ ID NO 24
<211> LENGTH: 11
<212> TYPE: PRT
<213> ORGANISM: Mus sp.

<400> SEQUENCE: 24

Asp Arg Tyr Thr Ala Val Ala Met Pro Met Leu
1               5                   10

<210> SEQ ID NO 25
<211> LENGTH: 11
<212> TYPE: PRT
<213> ORGANISM: Rattus sp.

<400> SEQUENCE: 25

Asp Arg Tyr Thr Ala Val Val Met Pro Val His
1               5                   10

<210> SEQ ID NO 26
<211> LENGTH: 11
<212> TYPE: PRT
```

<213> ORGANISM: Bos sp.

<400> SEQUENCE: 26

Glu Arg Trp His Thr Ile Thr His Ala Met Gln
1               5                   10

<210> SEQ ID NO 27
<211> LENGTH: 11
<212> TYPE: PRT
<213> ORGANISM: Mus sp.

<400> SEQUENCE: 27

Asp Arg Ser Leu Ala Ile Thr Gln Pro Leu Ala
1               5                   10

<210> SEQ ID NO 28
<211> LENGTH: 11
<212> TYPE: PRT
<213> ORGANISM: Mus sp.

<400> SEQUENCE: 28

Asp Arg Tyr Arg Ser Val Gln Gln Pro Leu Arg
1               5                   10

<210> SEQ ID NO 29
<211> LENGTH: 11
<212> TYPE: PRT
<213> ORGANISM: Homo sapiens

<400> SEQUENCE: 29

Asp Arg Tyr Cys Ala Val Met Asp Pro Leu Arg
1               5                   10

<210> SEQ ID NO 30
<211> LENGTH: 11
<212> TYPE: PRT
<213> ORGANISM: Mus sp.

<400> SEQUENCE: 30

Glu Arg Trp His Thr Ile Thr Tyr Ala Val Gln
1               5                   10

<210> SEQ ID NO 31
<211> LENGTH: 11
<212> TYPE: PRT
<213> ORGANISM: Rattus sp.

<400> SEQUENCE: 31

Asp Arg Tyr Ile Ala Val Cys His Pro Val Lys
1               5                   10

<210> SEQ ID NO 32
<211> LENGTH: 11
<212> TYPE: PRT
<213> ORGANISM: Bos sp.

<400> SEQUENCE: 32

Glu Arg Tyr Val Val Val Cys Lys Pro Met Ser
1               5                   10

<210> SEQ ID NO 33
<211> LENGTH: 11
<212> TYPE: PRT
<213> ORGANISM: Rattus sp.

```
<400> SEQUENCE: 33

Asp Arg Cys Leu Ala Ile Cys Gln Pro Leu Arg
1               5                   10

<210> SEQ ID NO 34
<211> LENGTH: 11
<212> TYPE: PRT
<213> ORGANISM: Rattus sp.

<400> SEQUENCE: 34

His Arg Cys Leu Gly Val Leu Arg Pro Leu His
1               5                   10

<210> SEQ ID NO 35
<211> LENGTH: 11
<212> TYPE: PRT
<213> ORGANISM: Mus sp.

<400> SEQUENCE: 35

Glu Cys Trp Leu Ser Leu Gly His Pro Phe Phe
1               5                   10

<210> SEQ ID NO 36
<211> LENGTH: 11
<212> TYPE: PRT
<213> ORGANISM: Rattus sp.

<400> SEQUENCE: 36

Glu Arg Cys Val Gly Val Thr Gln Pro Leu Ile
1               5                   10

<210> SEQ ID NO 37
<211> LENGTH: 11
<212> TYPE: PRT
<213> ORGANISM: Homo sapiens

<400> SEQUENCE: 37

Asp Arg Tyr Leu Ala Val Val His Pro Ile Lys
1               5                   10

<210> SEQ ID NO 38
<211> LENGTH: 11
<212> TYPE: PRT
<213> ORGANISM: Rattus sp.

<400> SEQUENCE: 38

Glu Arg Tyr Ile Ala Ile Cys His Pro Ile Lys
1               5                   10

<210> SEQ ID NO 39
<211> LENGTH: 11
<212> TYPE: PRT
<213> ORGANISM: Unknown
<220> FEATURE:
<223> OTHER INFORMATION: Sequence source uncertain: Vasopresin 1A
      receptor

<400> SEQUENCE: 39

Asp Arg Tyr Ile Ala Val Cys His Pro Leu Lys
1               5                   10

<210> SEQ ID NO 40
<211> LENGTH: 41
<212> TYPE: DNA
<213> ORGANISM: Artificial sequence
```

```
<220> FEATURE:
<223> OTHER INFORMATION: amino-terminal primer

<400> SEQUENCE: 40
gatactgggc tatccaagct tatgagcctc cccaattcct c                              41

<210> SEQ ID NO 41
<211> LENGTH: 42
<212> TYPE: DNA
<213> ORGANISM: Artificial sequence
<220> FEATURE:
<223> OTHER INFORMATION: carboxyl-terminal primer

<400> SEQUENCE: 41
aaggaaaaaa gcggccgctg gagcgaatat gcagaattct ct                             42

<210> SEQ ID NO 42
<211> LENGTH: 41
<212> TYPE: DNA
<213> ORGANISM: Artificial sequence
<220> FEATURE:
<223> OTHER INFORMATION: amino-terminal primer

<400> SEQUENCE: 42
aaggaaaaaa gcggccgcat gactctggag tccatgatgg c                              41

<210> SEQ ID NO 43
<211> LENGTH: 39
<212> TYPE: DNA
<213> ORGANISM: Artificial sequence
<220> FEATURE:
<223> OTHER INFORMATION: carboxyl-terminal primer

<400> SEQUENCE: 43
atgaaaccgc tcgagtcaca ccaggttgta ctccttcag                                 39

<210> SEQ ID NO 44
<211> LENGTH: 10
<212> TYPE: PRT
<213> ORGANISM: Artificial sequence
<220> FEATURE:
<223> OTHER INFORMATION: c-myc epitope

<400> SEQUENCE: 44

Glu Gln Lys Leu Ile Ser Glu Glu Asp Leu
1               5                   10

<210> SEQ ID NO 45
<211> LENGTH: 8
<212> TYPE: PRT
<213> ORGANISM: Artificial sequence
<220> FEATURE:
<223> OTHER INFORMATION: FLAG epitope

<400> SEQUENCE: 45

Asp Tyr Lys Asp Asp Asp Asp Lys
1               5
```